United States Patent
Timms

(10) Patent No.: US 6,309,843 B1
(45) Date of Patent: *Oct. 30, 2001

(54) GLYCOPROTEIN FOR USE IN DETERMINING ENDOMETRIAL RECEPTIVITY

(75) Inventor: Kathy Lynn Timms, Columbia, MO (US)

(73) Assignee: The Curators of the University of Missouri, Columbia, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/156,340

(22) Filed: Sep. 18, 1998

Related U.S. Application Data

(63) Continuation-in-part of application No. 08/328,905, filed on Oct. 25, 1994, now Pat. No. 5,831,035.

(51) Int. Cl.$^7$ ........................ G01N 33/53; G01N 33/573; A61B 17/425
(52) U.S. Cl. ..................... 435/7.1; 435/7.21; 435/7.4; 435/7.92; 435/7.95; 435/23; 436/503; 436/518; 436/536; 436/65; 436/87; 436/906; 530/388.24; 530/388.26; 530/389.1; 530/389.2; 600/551; 600/33; 600/34
(58) Field of Search ................................ 435/7.21, 7.4, 435/23, 7.92, 7.95, 7.1; 436/501, 503, 510, 518, 536, 65, 87, 814, 906; 600/551, 33, 34; 530/388.2, 388.24, 388.26, 389.1, 389.2; 424/9.2

(56) References Cited

U.S. PATENT DOCUMENTS

| | | |
|---|---|---|
| 4,564,362 | 1/1986 | Burnhill . |
| 4,666,828 | 5/1987 | Gusella . |
| 4,683,202 | 7/1987 | Mullis . |
| 4,703,752 | 11/1987 | Gabbay . |
| 4,801,531 | 1/1989 | Frossard . |
| 4,922,928 | 5/1990 | Burnhill . |
| 5,037,805 | 8/1991 | Ling . |
| 5,192,659 | 3/1993 | Simons . |
| 5,272,057 | 12/1993 | Smulson, et al. . |
| 5,395,825 | 3/1995 | Feinberg et al. . |
| 5,583,129 | 12/1996 | Spona et al. . |
| 5,756,115 | 5/1998 | Moo-Young et al. . |
| 5,771,900 | 6/1998 | Austin et al. . |
| 5,831,035 | * 11/1998 | Timms ................... 530/389.1 |

OTHER PUBLICATIONS

Maclaughlin et al., 1986. Two-dimensional gel electrophoresis of endometrial protein in human uterine fluids: qualitative and quantitative analysis. Biology of Reproduction 34: 579–585, 1986.*

Sharpe et al., Jun. 1994. Immunolocalization of progesterone–induced uterine protein, PUP–1, in human endometrium and endometrial and stromal cell cultures. Biology of Reproduction 50(Suppl. 1):61, Abstract #26.*

Bell, SC "Purification of human secretory pregnancy–associated . . . " Hum Reprod 1:313–18, (1986).

Bolen et al. "Reactive and neoplastic serosal tissue. A light–microscopic, ultrastructural and immunocytochemical study" Am J Surg Path 10:34–47 (1986).

Haining et al., "Epidermal growth factor in human endometrium: proliferative effects in culture and immunocytochemical . . . " Hum Reprod 6:1200–5 (1991).

Isaacson et al., "Production and secretion of complement component 3 by endometriotic tissue" J Clin Endocrin Metab 69:1003–9 (1989).

Kruitwagen et al., "Immunocytochemical marker profile of endometriotic epithelial, endometrial epithelia, and mesothelial cells . . . " European J Obstet Gynecol Reprod Biol 41:215–223 (1991).

Lessey et al., "Immunohistochemical analysis of estrogen and progesterone receptors in endometrisosis: comparison with normal . . . " Fertil Steril 51:409–415 (1989).

Melega et al., "Tissue factors influencing growth and maintenance of endometriosis" Ann NY Acad Sci 622:257–65 (1991).

Telimaa et al., "Elevated serum levels of endometrial secretory protein PP14 in patients with advanced endometriosis" Am J Obstet Gynecol 161:866–71 (1989).

Vernon et al., "Classification of endometriotic implants by morphologic appearance and capacity to synthesize prostaglandin F" Fertil Steril 801–806 (1985).

Vierikko et al., "Steroidal regulation of endometriosis tissue: lack of induction of . . . " Fertil Steril 43:218–224 (1985).

Daly et al, Prolactin production during in vitro decidualization of proliferative endometrium, 1983; Am J Obstet Gynecol 145:672–8.

(List continued on next page.)

Primary Examiner—James L. Grun
(74) Attorney, Agent, or Firm—Kohn & Associates

(57) ABSTRACT

An isolated and purified glycoprotein designated PUP-1 and functional analogs thereof are disclosed and characterized by being a progesterone induced and estradiol inhibited secretory glycoprotein from stromal cells of endometrial origin; having an N-terminal amino acid sequence as set forth in SEQ ID No:1; having a molecular weight of 70,000 daltons and an isoelectric point of 5.7; and synthesized by endometrium at the time of fertilization, early embryogenesis, and implantation. The present invention further provides a method of determining endometrial receptivity, monitoring placental physiology during gestation, and monitoring the effects of protocols to induce ovarian hyperstimulation or ovulation induction on uterine receptivity by monitoring the cyclic presence of PUP-1 in bodily fluid and tissue samples.

4 Claims, 2 Drawing Sheets

OTHER PUBLICATIONS

Seppala et al, Endometrial proteins: A reappraisal. Human Reprod 1992; 7:31–8.

Angell et al, "Chromosome abnormalities in human embryos after in vitro fertilization" Nature, 303:336 (1987).

Arthur et al, "Variations in concentrationS of the major endometrial secretory proteins (placental protein 14 and insulin–like growth factor binding protein–1) in assisted conception regimes" Human Reprod, 10:664–7 (1995).

Barkai et al, "Inhibition of Decidual Induction in Rats by Clomiphene and Tamoxifen" Biol Reprod, 46:733–39 (1992).

Beier, "Uteroglobin: A hormone–sensitive endometrial protein involved in blastocyst development" Biochem Biophys Acta, 160:289 (1968).

Birkedal–Hansen et al, "Matrix Metalloproteinases: A Review" Critical Reviews in Oral Biol, 4:197–250 (1993).

Chamberlin and Menino, "Partial Characterization of Gelatinases Produced by Preimplantation Porcine Embryos" Biol Reprod, 52:179, Abstract 492 (1995).

Cohen, "The effeciency and efficacy of IVF and GIFT" Human Reprod, 6:613–18 (1991).

Cornillie et al, "Expression of endometrial protein PP14 in pelvic and ovarian endometriotic implants". Hum Reprod 1991; 6:1141–1415.

Chritchley et al, "Role of the ovary in the synthesis of placental protein–14". J Clin Endocrinol Metab 1992; 75:97–100.

Edwards, "Normal and Abnormal Implantation in the Human Uterus" Implantation of the Human Embryo, Academic Press, Inc. London, 1:303–12, (1985).

Fazleabas et al, "Effect of Clomiphene citrate on the synthesis and release of the human b–lactoglobulin homologue, pregnancy associated endometrial $a_2$–globulin, by the uterine endometrium" Human Reprod, 6:783–90 (1991).

Fossum et al, "Ovarian Hyperstimulation Inhibits Embryo Implantation in the Mouse" J In Vitro Fertil Embryo Trans, 6:7–10 (1989).

Garbisa et al, "Cultured human trophoblast cells reproduce the initial events of placental biology" Clin Exp Obst Gyn 4:207–215 (1993).

Giudice, "Growth factors and growth modulators in human uterine endometrium: their potential relevance to reproductive medicine" Fertil Steril, 61:1–17 (1994).

Godkin et al, "Ovine Trophoblast Protein 1, an Early Secreted Blastocyst Protein, Binds Specifically to Uterine Endometrium and Affects Protein Synthesis" Endocrinology, 114:120–30 (1984).

Hampton and Salamonsen, "Expression of Messenger Ribonucleic Acid Encoding Matrix Metalloproteinases and Their Tissue Inhibitors is Related to Menstruation"J Endocrin, 141:R1–R3, (1994).

Hillam et al, Local antibody production aginst the murine toxin of Yersinia pestis in a golf ball–induced granuloma. 1974; Infect Immun 10:458–463.*

Jones et al, "Pathophysiology of reproductive failure after Clomiphene–induced ovulation", Am J Obstet Gynecol, 108:847–67 (1970).*

Joshi et al. Detection and synthesis of a progestagen–dependent protein in human endometrium. J Reprod Fertil 1980; 59:273–85.*

Joshi, "Progestin–dependent human endometrial protein: a marker for monitoring human endometrial function". Adv Exp Med Biol 1986; 230:167–86.*

Julkunen et al. Identification by hybridization histochemistry of human endometrial cells expressing mRNA's encoding a uterine β–lactoglobulin homologue and an insulin–like growth factor binding protein–1. Mol Endocrinol 1990; 4:700–7.*

Julkunen et al. Complete amino acid sequence of human placental protein 14: a progesterone–regulated uterine protein homologous to beta–lactoglobulins. Proc. Natl Acad Science USA 1988; 85:8845–49.*

Kawasaki, "PCR Protocols: A Guide to Methods and Applications" (Innis, et al, editors), Academic Press, Inc. (1990).*

Knudsen, "Proteins transferred to nitrocellulose as immunogens". 1985; Anal Biochem 147:285–288.*

Koistinen et al. Placental protein 12 is a decidual protein that binds somatomedin and has an identical N–terminal amino acid sequence with somatomedin–binding protein from human amniotic fluid. Endocrinology 1990; 118;1475–8.

Lifsey et al, "Isolation, Characterization and Imunocytochemical Localization of Bovine Trophoblast Protein–1" Biol Reprod, 40:343–52 (1989).

Lindley, "Life and death before birth" Editorial, Nature, 280:635–7 (1979).

Maslar and Riddick, "Prolactin production by human endometrium during the normal menstrual cycle". 1979. Am J Obstet Gynecol 1979; 135:751–4.

Matrisian et al, "Metalloproteinase Expression and Hormonal Regulation during Tissue Remodeling in the Cycling Human Endometrium" Extracellular Matrix in the Kidney, 107:94–100, Koide H. Hayashi, T (eds) Contrib. Nephrol. Basel, Karger (1994).

McRae et al. Immunohistochemical identification of prolactin and 24K protein in secretory endometrium. Fertil Steril 1986: 45:643–48.

Mulholand and Villie, "Proteins synthesized by the rat endometrium during early pregnancy" J Reprod Fertil, 72:395–400 (1984).

Navot et al, "Hormonal Manipulation of Endometrial Maturation" J Clin Endocrinol Metabol, 68:801–7 (1989).

O'Neill et al, "Use of a bioassay for embryo–derived platelet–activating factor as a means of assessing quality and pregnancy potential of human embryos" Fertil Steril, 47:969–75 (1987).

O'Neill et al, "Maternal Blood Platelet Physiology and Luteal–Phase Endocrinology as a Means of Monitoring Pre–and Postimplantation Embryo Viability Following in Vitro Fertilization" J In Vitro Fertil Embryo Transfer, 2:87–93 (1985).

Osteen et al. Development of a method to isolate and culture highly purified populations of stromal and epithelial cells from human endometrial biopsy specimens. Fertil Steril 1989: 52:965–72.

Paulson et al, "Embryo implantation after human in vitro fertilization: importance of endometrial receptivity" Fertil Steril, 53:870–74 (1990).

Psychoyos, "Endocrine control of egg implantation" in Handbook of Physiology, Chap 40:187–215 Greep RO, Astwood EG, Geiger SR (eds), Washington, DC, American Physiological Society, (1973).

RiittineN, "Serous ovarian cyst fluids contain high levels of endometrial placental protein 14". Tumor Biol 1992; 13:175–9.

Roberts, "Conceptus Interferons and Maternal Recognition of Pregnancy" [Review] Biol Reprod, 40:449–52 (1989).

Roberts and Bazer, "The properties, function and hormonal control of synthesis of uteroferrin, the purple protein of the pig uterus" in Steroid Induced Proteins, p. 133, edited by M. Beato, Holland, Amsterdam Elsevier–North (1980).

Roberts and Lowe, "Where have all the conceptions gone?" Lancet, 1:498–501 (1975).

Roberts et al, "Interferons at the placental interface" [Review] J Reprod Fertil, 41:63–74 (Supp, 1990).

Rodgers et al, "Patterns of Matrix metalloproteinase Expression in Cycling Endometrium Imply Differential Functions and Regulation By Steroid Hormones" J Clin Invest, 94:946–53 (1994).

Safro et al, "Elevated luteal phase estradiol:progesterone ratio in mice causes implantation failure by creating a uterine environment that suppresses embryonic metabolism" Fertil Steril, 54:1150–53 (1990).

Seppala et al, "Human endometrial protein secretion relative to implantation" Bailliere's Clinic Obstet Gynecol, 5:61–72 (1991).

Seppala et al, "Uterine proteins, nomenclature determined by biological action" Res in Reprod, 19:2 (1987).

Sharma et al, "Influence of superovulation on endometrial and embryonic development" Fertil Steril, 53:822–29 (1990).

Sharpe et al. Detection of a progesterone–induced secretory protein synthesized by the uteri but not the endometriotic implants of rats with induced endometriosis. Fertil Steril 1991: 55:403–10.

Sharpe et al. Proliferative and morphogenic changes induced by the coculture of rat uterine and peritoneal cells: a cell culture model for endometriosis. Fertil Steril 1992; 58:1220–9.

Sharpe and Vernon, Polypeptides synthesized and released by rat endometriotic tissue differ from those of the uterine endometrium in culture. Biol Reprod. 1993a; 48:1334–1340.

Sharpe et al. Polypeptides synthesized and released by human endometriosis tissue differ from those of the uterine endometrium in cell and tissue explant culture. Fertil Steril 1993b; 60:839–51.

Sharpe et al. Synthesis and secrection of the progesterone–induced uterine protein, PUP–1, during early pregnancy in the rat. Soc Study of Reprod, 1993; P–233, Fort Collins, CO.

Sharpe, et al. Immunohistochemical localization of the progesterone–induced uterine protein, PUP–1, in the human decidua and trophoblast during gestation. Amer Fertil Soc, 1994, abstract.

Sharpe and Zimmer, "Effects of the progesterone antagonist Onapristone (ZK 98.299) on synthesis and secretion of the progesterone uterine protein, PUP–1, in the rat" Amer Fertil Soc, p. 271, Montreal, Quebec, Canada (1993).

Sharpe et al, "Rapid regression of endometriosis by a new gonadotropin–releasing hormone antagonist in rats with surgically induced disease" in Current Concepts in Endometriosis, p. 449–58, edited by DP Chada and VC Buttram, Alan R. Liss, Inc., New York (1990a).

Sharpe et al, "Follicular Atresia and Infertility in Rats Treated with a Gonadotropin–Releasing Hormone Antagonist" Endocrinology, 127:25–31, (1990b).

Sharpe–Timms et al, "Immunolocalization of progesterone–induced uterine protein–1 in human endometerium during the menstrual cycle and in the placenta throughout gestation" Am J Obstet Gynecol, 173:1569–78 (1995a).

Sharpe–Timms, et al, "Partial purification and amino acid sequence analysis of rat and human progesterone–induced uterine protein–1 reveals homology with 72kDa Gelatinase A" Soc Gyn Invest Abstract Form (1995b).

Sharpe–Timms, et al, "Partial purification and subsequent amino acid sequence analysis of endometriosis protein group–2 (endo–2) reveals homology with tissue inhibitor of metalloproteinases–1 (TIMP–1)" Soc Study Repro Abstract Form (1995c).

Smith, "Growth factors in the human endometrium" Human Reproduction Update, 9:936–46 (1994).

Tabibzadeh, "Cytokines and the hypothalamic–pituitary–ovarian–endometrial axis" Human Reproduction Update, 9:947–67 (1994).

Wahlstrom and Seppala. Placental protein 12 (PP12) is induced in the endometrium by progesterone. Fertil Steril 1984; 41;781–4.

Weibel, "Stereological Methods". In: Practical Methods for Biological Morphometry, vol. 1, New York: Academic Press; 1979;33–45.

Woessner, "Matrix metallopreteinases and their inhibitors in connective tissue remodeling" FASEB, 5:2145–54 (1991).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 30 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
       (A) ORGANISM: Homo sapiens (xi) SEQUENCE DESCRIPTION: SEQ ID NO:1:

```
Tyr Pro Leu Asp Gly Ala Ala Arg Gly Glu Asp Thr Ser Met Asn Leu
1               5                   10                  15

Val Gln Lys Tyr Leu Glu Asn Tyr Tyr Asp Leu Xaa Lys Asp
            20                  25                  30
```

(2) INFORMATION FOR SEQ ID NO:2:

(i) SEQUENCE CHARACTERISTICS:
       (A) LENGTH: 22 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
       (A) ORGANISM: Rat (xi) SEQUENCE DESCRIPTION: SEQ ID NO:2:

```
Tyr Pro Leu His Arg Ser Glu Glu Asp Ala Leu Thr Glu Val Leu Gln
1               5                   10                  15

Asp Tyr Leu Xaa Asn Tyr
            20
```

GLYCOPROTEIN FOR USE IN DETERMINING ENDOMETRIAL RECEPTIVITY

CROSSREFERENCE TO RELATED APPLICATIONS

This application is a continuation-in-part of U.S. Ser. No. 08/328,905 filed Oct. 25, 1994, now U.S. Pat No. 5,831,035.

GOVERNMENT SUPPORT

The research carried out in connection with this invention was supported in part by a grant from the National Institute of Health No. DHHS NICHD R29HD29026. The Government has certain rights in this invention.

BACKGROUND OF THE INVENTION

1. Field of the Invention

The present invention relates to human fertility and more particularly, to means and methods for determining uterine endometrial receptivity for a fertilized egg and a method and composition for contraception.

2. Description of Related Art

There are many issues involved with the evaluation of a woman's fertility. Production and availability of an egg, fertilization of the egg, and other issues involving the physiology of the egg are involved. Another general issue is the nature of the receptivity of the endometrium. If not receptive to implantation, implantation of a fertilized egg may not occur or may occur in an abnormal manner. If receptive, implantation is optimized. Accordingly, it would be useful to have a diagnostic tool for determining endometrial receptivity.

Reproductive Failure and Assisted Reproductive Technologies: In 1975, Roberts and Loewe, using a mathematical equation, suggested that 78% of fertilizations fail to result in a live birth [Roberts and Loewe, 1975]. Lindley [1979] estimated that only about 30% of all conceptions survive to birth, 15% end in recognizable miscarriage, and the other 55% are lost in the early stages of pregnancy. Inadequate uterine receptivity and subsequent embryo implantation failure, rather than fertilization failure, has been implicated as the crucial event which differentiates fertile and nonfertile ovulatory cycles [Navot et al., 1989]. The importance of endometrial adequacy and receptivity has become even more apparent with the evolution of the assisted reproductive technologies. In vitro fertilization and embryo transfer procedures produce fertilization rates of 70 to 90% whereas pregnancy rates after embryo transfer remain disappointing low ranging from 15 to 25% [Edwards, 1985; Cohen, 1991]. Ovarian hyperstimulation protocols used for these procedures have been associated with several factors that may contribute to lower implantation rates including production of oocytes and subsequent embryos that are chromosomally unbalanced, creation of embryos that are biochemically defective and alteration of the maternal uterine environment [Angell et al., 1987; O'Neill et al., 1987; Collier et al., 1989; Safro et al., 1990]. An improved knowledge of factors influencing maternal uterine environment and human embryo implantation may help "save" these embryos and reduce embryo loss.

Studies have demonstrated that ovarian hyperstimulation impedes implantation by causing adverse changes in uterine receptivity [Fossum et al., 1989; Paulson et al., 1990; Sharma et al., 1990]. For example, clomiphene citrate, an antiestrogen widely used for ovarian hyperstimulation, has been linked to lower conception rates, a higher incidence of spontaneous abortion and might be partially responsible for deficiencies in endometrial development [Jones et al., 1970]. Clomiphene citrate inhibits decidual induction in pseudopregnant rats when administered prior to pyrathiazine injection (induces decidualization in rats) and inhibits implantation of rat blastocysts when administered at the time of their adherence to the uterus [Barkai et al., 1992]. This inhibition could not be explained on the basis of the current understanding of mechanisms of estrogen action. Fazleabas et al. [1991] demonstrated that clomiphene citrate markedly decreased endometrial $\alpha_2$-pregnancy associated endometrial globulin ($\alpha_2$PEG; also called placental protein 14 or PP14 or progesterone dependent endometrial protein, PEP) production in vitro. Arthur and colleagues [1995] have shown that PP14 concentrations are depressed and insulin-like growth factor binding protein-1 (IGFBP-1 originally called $\alpha_1$PEG or PP12) concentrations are elevated in pregnancies that follow down-regulation of the anterior pituitary (Buserelin, Hoechst, Hounslow, UK) and exogenous hormone support (Pergonal, Serono, Welwyn Garden City, UK) prior to a frozen-thawed embryo transfer. No correlation could, however, be found between hCG, IGFBP-1, progesterone and PP14 concentrations suggesting no primary associations between these compounds.

The above studies demonstrate that ovarian hyperstimulation/ovulation induction protocols alter normal endometrial development and protein synthesis. Unfortunately, no noninvasive methods or markers have yet been developed to detect the effects of these protocols on subsequent uterine receptivity. An accurate marker for uterine receptivity for blastocyst implantation is urgently needed as a clinical adjuvant in assisted reproduction procedures and may improve the pregnancy rate in women who have experienced difficulty in conceiving due to an anomalous state of uterine receptivity and implantation failure.

The efficiency of implantation in assisted reproduction procedures in quite low. Presently, three to four high quality cleavage stage embryos are transferred to the uterus following in vitro fertilization. Routinely, such embryo transfers result in a singleton pregnancy in approximately 15 to 25% of the patients. Higher risk, multiple gestations do result from these transfers. Improved knowledge of factors influencing human embryo implantation and an accurate marker of uterine receptivity would help reduce embryo loss by reducing the numbers of embryos needed for transfer and reducing the potential for multiple gestation. The need for fewer embryos may also reduce the amount of exogenous ovarian stimulation needed and thereby reduce risks associated with taking these compounds. The need for reduced numbers of embryos may be most important in reproductively older women (>38 years of age) who frequently are approaching the menopause and are producing fewer quality ooctyes and consequently fewer embryos.

An accurate marker would permit monitoring of the state of uterine receptivity prior to embryo transfer. Embryo transfer procedures could be timed to coincide with a receptive endometrium or delayed, cryopreserving embryos, until a more appropriate state of receptivity was attained. This may be especially relevant in patients where ovarian hyperstimulation and ovulation induction has altered the natural course of endometrial development. A marker of uterine receptivity may also be diagnostic in women who repeatedly fail to become pregnant and whom have no other apparent etiology for their infertility.

An accurate marker for uterine receptivity may also help reduce the cost of infertility procedures. The cost of assisted reproductive procedures varies across the United States (estimated ranges from $10,000 to $25,000 and higher for an in vitro fertilization/embryo transfer procedure). Often, infertility procedures are not covered by insurance. The most expensive portion of infertility therapies is usually the drugs. As stated above, if uterine receptivity can be defined by a marker and fewer embryos are needed, then less drug may also be needed thereby reducing the cost. Inadequate uterine receptivity could be diagnosed and possibly therapeutically enhanced prior to attempting or during assisted reproduction procedures thus requiring fewer overall attempts per conception.

The composition of uterine secretions is of considerable interest because of how they may effect reproductive processes such as sperm migration, embryo transport and implantation in the uterine endometrium. Uterine fluid, as it exists in vivo, is a mixture of proteins synthesized and secreted by the endometrium, proteins transferred across the endometrium from the blood stream or adjacent cells and proteins from the oviduct and/or cervix. As a result of progesterone (P) stimulation, the secretory stage human endometrium synthesizes and secretes specific proteins including pregnancy-associated endometrial $\alpha_1$-globulin ($\alpha_1$-PEG) pregnancy-associated endometrial $\alpha_2$-globulin ($\alpha_2$-PEG), prolactin (PRL) and progesterone-induced uterine protein-1 (PUP-1)[Seppela et al., 1992; Maslar and Riddick, 1979; Sharpe et al., 1993]. Although $\alpha_1$-PEG has been described by different names in the literature including placental protein 12 (PP12) and endometrial protein 14 (EP14), subsequently analysis has identified this protein as insulin-like growth factor binding protein-1 (IGFBP-1) [Koistinen et al., 1992].

Preimplantation development and communication: embryo/endometrium cross-talk: Factors secreted by sheep and cattle conceptuses that are structurally related to interferons (IFNs) have been identified (ovine trophoblastic protein-1 and bovine trophoblastic protein-1) and implicated as mediators of maternal recognition of pregnancy [Godkin et al., 1984; Lifsey et al., 1989]. The fact that preimplantation conceptuses of other species, e.g. pig, release substances with antiviral activity suggests the IFNs may play a role in pregnancy that extends beyond domestic ruminants [Roberts, 1989; Roberts et al., 1990]. Embryos also produce platelet activating factor (PAF) which is capable of inducing transient maternal thrombocytopenia [O'Neill et al., 1985]. Embryo PAF is being evaluated as a means of monitoring pre- and post-implantation embryo viability following in vitro fertilization. Two gelatinases (also called matrix metalloproteinase: MMP2 and MMP9) produced by porcine embryos during the preimplantation period may be involved in the dramatic changes in endometrial morphology that occur during this period [Chamberlin and Menino, 1995]. Despite this accumulation of knowledge, surprisingly scant information about mechanisms controlling the receptive phase of the uterine endometrium and subsequent blastocyst implantation is available.

For more than two decades it has been known that synchronized development of the preimplantation embryo and hormonal preparation of the uterus to the receptive state were essential for initiation of pregnancy and subsequent decidualization of the uterine stroma [Psychoyos, 1973]. Glandular and luminal endometrial epithelia require estrogen while endometrial stroma requires both estrogen and progesterone for proliferation and differentiation. More recent concepts have emerged including mediation of estrogen and progesterone action in the endometrium by specific growth factors, growth factor receptors, cytokines, enzymes and their inhibitors [Giudice, 1994; Smith, 1994; Tabibzadeh, 1994; Rodgers et al., 1994]. For example, studies have documented expression of matrix metalloproteinases (MMPs) and their inhibitors in the human endometrium [Rodgers et al., 1994; Hampton and Salamonsen, 1994; Matrisian et al., 1994]. These studies have demonstrated the requirement for a balance between the expression of MMPs and their inhibitors in the continual processes of growth, differentiation and destruction of the endometrium that occur throughout the menstrual cycle. Production of MMPs by both the embryo and the endometrium suggests a possible mechanism of cross-talk and regulation of the process of implantation by these two entities.

Uterine protein content increases during the preimplantation period in most mammalian species. These increases are due to decreasing water content and increasing viscosity due to the influence of progesterone. Progesterone also stimulates the synthesis and secretion of specific endometrial proteins in several mammalian species including the human [i.e., Mulholand and Villie, 1984; Sharpe et al., 1991; Sharpe and Vernon, 1993; Sharpe et al., 1993]. The functions of some of these proteins such as uteroglobin from the rabbit endometrium (immunomodulation of fetomaternal interactions) and uteroferrin in the pig (placental iron transport) have been defined [Beier, 1968; Roberts and Bazer, 1980]. In the human, $\alpha_1$-PEG has been identified as insulin-like growth factor (IGF-I) binding protein while the sequence of $\alpha_2$-PEG indicates homology to $\beta$-lactoglobulin (up to 53%) and human retinol binding protein (23%) and may serve an immunoregulatory role or as a transfer protein [Seppala et al., 1987; Seppala et al., 1991]. Endometrial prolactin (PRL) production is also stimulated by progesterone in the human uterus [Maslar and Riddick, 1979]. Disappointingly, and for various reasons, none of these proteins has yet been proven useful for prediction of uterine receptivity and successful embryo implantation.

Messenger RNA encoding human IGFBP-1 and corresponding protein has been identified in secretory stage endometrial stromal cells but not secretory stage epithelial cells nor any proliferative stage endometrial cells [Julkunen et al., 1990; Wahlstrom et al, 1984]. Studies of the amino acid sequence of these immunologically indistinguishable proteins have demonstrated significant sequence homology with $\beta$-lactoglobulins [Julkunen et al., 1990].

Immunolocalization of $\alpha_2$-PEG, PP14 and PEP has been demonstrated in secretory stage glandular epithelium but not the stroma [Sharpe et al., 1993; Joshi et al., 1980, 1986]. Prolactin is synthesized by P-stimulated endometrial stromal cells and immunolocalizes in subpopulations of late secretory stage decidualized stromal cells and in epithelial cells [Maslar and Riddick, 1989; Daly et al., 1983; McRae et a. 1986]. While, these are known, there is no clinical utility for these proteins that would serve as a marker for endometrial receptivity and therefore fertility or infertility.

Therefore it is desirable to obtain means and a method for determining endometrial receptivity based on unique proteins synthesized and secreted by human endometrium in vitro and in vivo.

Improved methods of contraception, that is prevention of fertilization or implantation of the fertilized egg, are needed particularly in light of increasing population pressure. Many efforts have been made to provide improved contraception utilizing devices or hormonal therapy for females as for example as set forth in U.S. Pat. Nos. 5,771,900; 5,756,115; 5,583,129; 4,922,928; 4,703,752; and 4,564,362 and the references cited therein. However, they are not always successful in providing contraception and improved methods are needed. Progesterone receptor antagonists (such as RU486) alter uterine biochemistry but this alteration is used to induce abortion or as a morning-after pill to prevent implantation. It would be useful to have other methods available which can change uterine receptivity biochemcially.

SUMMARY OF THE INVENTION

In accordance with the present invention, there is provided an isolated and purified human glycoprotein (designated herein as PUP-1) and functional analogs thereof characterized by (a) being progesterone induced and estradiol inhibited secretory glycoprotein specifically synthesized and secreted by stromal cells of endometrial origin;

(b) having an N-terminal amino acid sequence as set forth in SEQ ID No:1;

(c) having a molecular weight of 70,000 daltons as determined by two-dimensional sodium dodecyl sulphate polyacrylamide gel electrophoresis (SDS-PAGE);

(d) having an iso-electric point of 5.7; and (e) synthesized by endometrium at the time of fertilization, early embryogenesis, and implantation and being present in the uterine fluid and serum in a cycle presence as described herein.

The present invention further provides a method of determining uterine endometrial receptivity by first obtaining a serum, uterine fluid or endometrial biopsy sample from a patient and detecting the presence of the above-described glycoprotein, PUP-1, wherein the cyclic presence of PUP-1 as compared to non-receptive controls indicates uterine receptivity. In normal fertile human female controls the PUP-1 is present in uterine fluid and serum during the implantation window as well as immunohistochemically identified on the apical surface of the luminal epithelium of the endometrium. Where necessary for the evaluation, repetitive samples will be collected throughout the menstral cycle. Non-receptive controls are both women who are in the non-fertile stage of the menstrual cycle and women with known uterine dysfunction where PUP-1 is not present or persistantly present on the uterine luminal epithelium throughout the menstrual cycle.

PUP-1 concentrations in uterine biopsy tissue or fluid and sera vary between known fertile and infertile women during the window of implantation, deviate in women undergoing ovarian hyperstimulation/ovulation induction and correlate with successful initiation of pregnancy; therefore, PUP-1 serves as a minimally or noninvasive marker of uterine receptivity for blastocyst implantation.

The present invention further provides a method of monitoring the effects of ovarian hyperstimulation and/or ovulation induction protocols on uterine receptivity either for individual women receiving the treatment or for the evaluation of new protocols. The method includes the steps of (a) obtaining a serum, uterine or fluid or endometrial biopsy sample from a patient receiving the treatments and then (b) detecting the presence of a glycoprotein designated PUP-1 characterized by (i) being progesterone induced and estradiol inhibited secretory glycoprotein specifically from stromal cells of endometrial origin;

(ii) having an N-terminal amino acid sequence as set forth in SEQ ID No:1;

(iii) having a molecular weight of 70,000 daltons as determined by two-dimensional SDS-PAGE polyacrylamide gel electrophoresis;

(iv) having an isoelectric point of 5.7; and (v) synthesized by endometrium at the time of fertilization, early embryogenesis, and implantation; wherein cyclic presence of PUP-1 indicates receptivity. A disruption of the normal cyclic presence of PUP-1 indicates that the treatment is adversly affecting uterine receptivity. This disruption can include non-cyclic presence of PUP-1, no PUP-1 or an aberrant cyclic presence of PUP-1 as compared to controls.

The present invention further provides a method of contraception by interrupting the cyclic presence of PUP-1. The interruption can be to reduce or eliminate PUP-1 presence during the uterine receptivity window for implantation of the menstral cycle and to thereby alter the cyclic presence/pattern of PUP-1. The interruption can utilize an antagonist of the PUP-1 glycoprotein. The term antagonist or antagonizing is used in its broadest sense. Antagonism can include any mechanism or treatment which results in inhibition, inactivation, blocking or reductionn or alteration of cyclic presence of PUP-1.

DESCRIPTION OF THE DRAWINGS

Other advantages of the present invention will be readily appreciated as the same becomes better understood by reference to the following detailed description when considered in connection with the accompanying drawings wherein:

FIG. 3(B) endometrial epithelial cell culture, day 12, cytokeratin mAb ({open arrow}, three-dimensional mound of epithelial cells {closed arrowheads}, interconnecting tubular processes ×200); FIG. 3(C) endometrial stromal cell culture, day 8, vimentin mAb (×400); (FIG. 3D) endometriotic epithelial cell culture, day 6, BMA 180/cytokeratin mAbs (×200); (FIG. 3E) endometriotic epithelial cell culture, day 8, cytokeratin mAb (×400); (FIG. 3F) endometriotic stromal cell culture, day 8, vimentin mAb (×400).

DETAILED DESCRIPTION OF THE INVENTION

Figure 1A:
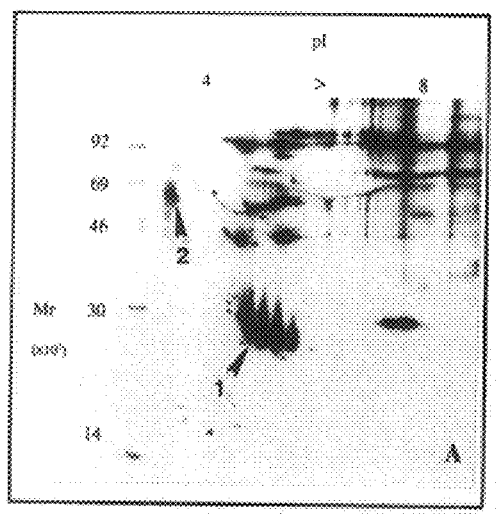
FIGS. 1A–1D are photographs of representative two-dimensional SDS-PAGE fluoragraphs of L-[$^{35}$S] methionine-labeled secretory proteins from secretory phase endometrial epithelial cell FIG. 1(A), endometrial stromal cell FIG. 1(B), endometriotic epithelial cell FIG. 1(C), and endometriotic stromal cell FIG. 1(D) culture media.
Figure 1B:
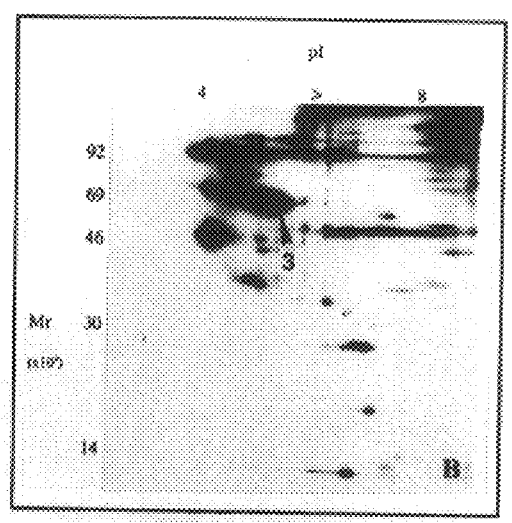
Figure 1C:
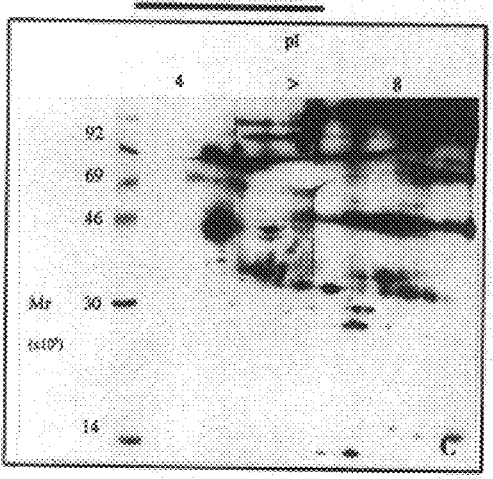
Figure 1D:
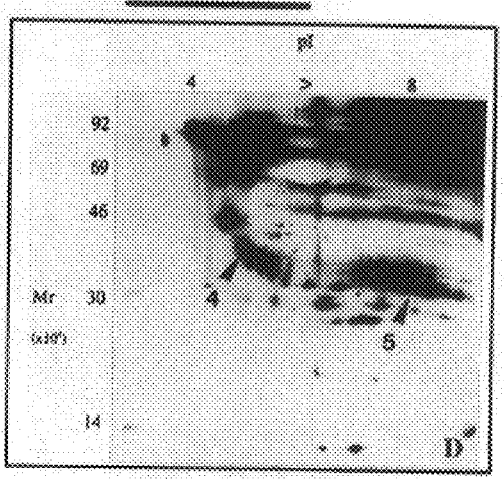

The present invention provides a purified and isolated glycoprotein generally designated herein PUP-1 and biologically functional analogs thereof being characterized by several critical and functional physical characteristics and a N-terminal amino acid sequence (SEQ ID No:1).

Physically, the glycoprotein has been characterized as a N-acetyl linked glycoprotein and appears to be a member of the matrix metalloproteinase (MMP) family of proteins. As described below in the experimental section, the glycoprotein, which is a member of the MMP family but generally referred to herein as PUP-1, has a molecular weight of 70,000 daltons as determined by two dimensional SDS-PAGE polyacrylamide gel electrophoresis. The glycoprotein has an isoelectric point (pI) of 5.7.

Applicant has determined the first amino acids of the N-terminal of human PUP-1 to be (SEQ ID No:1) YPLDGAARGEDTSMNLVQKY-LENYYDLXKD and the N-terminal sequence of rat PUP-1 to be (SEQ ID No:2) YPLHRSEEDALTEVLQDYLXNY as set forth in Example 4.

The isolated and purified glycoprotein of the present invention is secreted in a cyclic pattern as an endometrial product of endometrial stromal cell origin. In normal fertile human female controls the PUP-1 glcoprotein is present in uterine fluid and serum as well as immunohistochemically identified on the apical surface of the luminal epithelium of the endometrium only during the implantation window (Days 19–23). The glycoprotein is synthesized by the endometrium at the time of early embryogenesis and implantation. Additionally, as evidenced below, the PUP-1 glycoprotein is also detected in explant culture media from progesterone treated, but not estrogen treated stromal cells. As further evidenced below, culture media of isolated and purified endometrial stromal cells, but not epithelial cells, from human tissues produce the PUP-1 glycoprotein. Due to the timing of the synthesis of the PUP-1 glycoprotein by the endometrium, and its cyclic presence specifically at the time of the reproductive cycle which coincides with early embryogenesis, and implantation, PUP-1 protein is clinically useful in the evaluation of endometrial function, differentiation, and implantation as well as in the evaluation of luteal phase physiology.

As shown herein PUP-1 in a normal fertile female has the following cyclic presence during the 28 day menstrual cycle.

| Cycle Day | PUP-1 Presence in Uterine Fluid | PUP-1 Presence on apical surface of the luminal epithelium of the endometrium | PUP-1 Presence Summary |
|---|---|---|---|
| 0–5 start of menses | +/− (equivocal) | − | not present |
| 14 ovulation | − | − | not present |
| 19–23 implant window | + | + | present |
| 28 | − | +/− (equivocal) | not present |

The monitoring of PUP-1 also provides a method of monitoring the effects of treatments for ovarian hyperstimulation and/or ovulation induction on uterine receptivity. The cyclic localization of PUP-1 on the luminal epithelium of the uterine endometrium on menstrual cycle days 19–23±1 day defines the period of uterine receptivity for embryo implantation. This is shown in the examples by results with treatments of clomiphene citrate and gonadotropin stimulation. This method therefore provides an evaluation of methods as they are developed for ovarian hyperstimulation and/or ovulation induction on uterine receptivity. If the treatment induces a disruption of the normal cyclic presence of PUP-1 this indicates that the treatment is adversly affecting uterine receptivity. This disruption can include non-cyclic presence of PUP-1, no PUP-1 or an aberrant cyclic presence of PUP-1 as compared to controls.

PUP-1 concentrations in uterine fluid, cervical mucus and sera vary between known fertile and infertile women as shown in the Examples during the window of implantation, deviate in women undergoing ovarian hyperstimulation/ovulation induction and correlate with successful initiation of pregnancy; therefore, PUP-1 serves as a minimally or noninvasive marker of uterine receptivity for blastocyst implantation and as a marker for response to methods of ovarian hyperstimulation.

The N-acetyl linked glycoprotein, PUP-1, was isolated and purified by means well-known in the art as described in the experimental section below.

By biologically functional analogs, it is meant an analog will be generally at least 70% homologous over any portion that is functionally relevant. In more preferred embodiments the homology will be at least 80% and can approach 95% homology to the glycoprotein. Differences in glycosylation can provide analogs. The molecular weight of a glycoprotein can vary between the analog and the present invention due to carbohydrate differences. The analog will have the same biological function and presence and timing of appearance.

The term "progesterone induced and estradiol inhibited secretary glycoprotein" is used to indicate that at least in culture, PUP-1 is isolated and purified from endometrial stromal cells, but not epithelial cells by the addition of progesterone to the media for inducement and addition of estradiol for the media for inhibition.

As evidenced below, the purified isolated glycoprotein can be detected in endometrial biopsy specimens. According, since Applicant has provided experimental evidence of the synthesis, secretion and localization of PUP-1, specifically during the luteal phase, the time of endometrium receptivity, the present invention can provide a method of determining endometrial receptivity (menstrual cycle days 19–23±1 day). Generally, the method includes the steps of first obtaining a serum, uterine fluid or endometrial sample by methods well-known in the art. For example, serum may be collected by venipuncture into a red top tube. Endometrial tissue can be obtained using a Pipelle™ (Unimar, Wilton, Conn.) endometrial suction curette. Tissues are then transported to the laboratory in saline and the quantitative detection of the presence of the glycoprotein PUP-1 is undertaken.

The detection of the glycoprotein can be accomplished by various methods. The experimental data below demonstrate immunohistochemical localization of the PUP-1 protein. Immunohistochemical methods for such a detection are well-known in the art. The glycoprotein may be detected in formalin fixed, paraffin embedded tissues by immunohistochemistry using the avidin-biotin peroxidase method [Sharpe et al., 1994]. It is also advantageous to immunohistochemically stain the tissues sections for cytokeratin and prolactin to identify the specific cell populations. (See *Basic and Clinical Immunology* (Stites and Terr, eds., Seventh Edition) Appleton & Lange, Norwalk, Conn. (1991), pp 245–251 for a general discussion of immunohistochemical techniques). The glycoprotein may also be detected in sera or culture media of SDS-PAGE separated glycoproteins by Western blot analysis, a technology well known to those skilled in the art as described generally in Harlow and Lane, *Antibodies: A Laboratory Manual*, Cold Spring Harbor Laboratory, Cold Spring Harbor, N.Y., 1988; pp 475–501 and as used by the Applicant [Sharpe et al., 1993].

Applicant provides herein below immunochemical localization methods of the PUP-1 glycoprotein. To achieve the results, Applicant has developed polyclonal antibody made from de novo synthesized and purified PUP-1. This antibody is demonstrated to have clinical utility for the detection of the PUP-1.

Antibodies may be either monoclonal or polyclonal, in the preferred embodiment they are polyclonal. Antibodies may be generated from isolated, partially purified glycoprotein or, alternatively, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and as is described hereinbelow in the Examples for "off-blot" generation of antibody [Knudsen, 1985].

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination. In a preferred embodiment, the avidin-biotin peroxidase system is used.

As evidenced by the studies below, PUP-1 is specifically a product of secretory phase endometrial stromal cells and localizes in the decidua and trophoblast throughout gestation. Accordingly, PUP-1 can be clinically useful as a diagnostic marker for progesterone dependent endometrial/placenta functions/activity and physiology. Specifically, the experimental evidence below shows the isolated glycoprotein can be useful in the method to determine endometrial receptivity, the presence of the glycoprotein as compared to the nonreceptive stage of the cycle indicating endometrial receptivity. Further, the method also provides a means of determining if methods/treatments to induce ovulation or ovarian hyperstimulation have disrupted endometrial receptivity in individuals who are receiving such treatments as for example clomiphene citrate and/or gonadotropin stimulation. Additionally, the method of the present invention allows evaluation of the effects of other methods of ovulation stimulation on uterine receptivity by measurement of PUP-1 synthesis and timing of its presence as compared to fertile and non-fertile (non-receptive) controls. It should be noted that non-receptive controls are both women who are in the non-fertile stage of the menstrual cycle and women with known uterine dysfunction where PUP-1 is not present, aberrantly cyclicly present, or persistantly present throughout the menstrual cycle.

The method of the present invention can provide monitoring placental activity/physiology during gestation (see Example 3), particularly in women who have a history of miscarriages. The method includes the steps of obtaining a placental biopsy sample from a patient and detecting the presence of PUP-1 indicating continued placental physiology associated with PUP-1.

The determination of endometrial receptivity utilizing a biochemical marker is critical. A morphological analysis of the cells may determine structural indications of receptivity, but this does not necessarily mean that the endometrial cells are biochemically and functionally in phase. Preferably, the use of the glycoprotein marker, PUP-1, of the present invention identified in the biopsy or serum samples will provide critical information with regard to the functional receptivity of the endometrium for implantation and can be used in combination with structural analysis. This information in combination with other fertility factors is extremely useful in the analysis of fertility. Finally, such information can provide necessary information critical to therapy for infertility if needed as well as for in vivo contraception techniques.

As shown in the Examples herein below, progesterone-induced uterine protein-1, PUP-1, is synthesized and secreted by rat and human endometrial explants and endometrial stromal cells (but not endometrial epithelial cells) when tissues and cells are collected from either progesterone-treated or reproductively cyclic uteri during periods of elevated serum progesterone. Rat and human endometrial stromal cell PUP-1 synthesis and secretion is elevated in vitro in response to medroxyprogesterone acetate (MPA; Sharpe-Timms, unpublished). PUP-1 is present in culture media and uterine washings from uteri recovered from secretory phase, progesterone-treated and simulated pregnant baboons.

The physical presence of an embryo or substances produced by embryos may also affect synthesis and secretion of uterine proteins. Embryos produce several proteins which may participate in cross-talk with the endometrial proteins in preparation for implantation. Applicants have shown PUP-1 is synthesized and secreted by the rat uterus coinciding with the entry of fertilized oocytes, peaking around the time of implantation in the rat. Increased steroid concentrations associated with pregnancy (or pseudopregnancy) may also alter endometrial protein production. PUP-1 is present in uterine washings of simulated pregnant baboons (Example 5, herein below).

Applicants have demonstrated the pattern of PUP-1 localization in the endometrium and placenta throughout the menstrual cycle and pregnancy, respectively. Endometrial PUP-1 immunolocalization shifts from the stroma during the proliferative stage of the menstrual cycle to the stroma and glands during the early to mid-secretory stage of the cycle coinciding with the time of ovulation, fertilization, embryo cleavage and transport through the oviduct and implantation. PUP-1 dissipates from the nonpregnant, late-secretory endometrium yet persists and localizes in decidua and trophoblast during gestation. These observations show endometrial PUP-1 having an autocrine role in the process of endometrial differentiation and decidualization and/or a paracrine role to communicate between the endometrium and the preimplantation embryo and will be useful as a marker of uterine receptivity and blastocyst implantation.

The gonadotropin-releasing hormone (GnRH) analogue, Antide [N-Ac-D-2Nal$^1$, D-4-ClPhe$^{2+sc}$, $^D$-3-Pal$^3$, Nic-Lys$^5$, D-Nic-Lys$^6$, I-Lys$^8$, D-Ala$^{10}$], has the ability to suppress reproductive cyclicity in rats as noted from the analysis of systemic follicle stimulating hormone (FSH), estradiol and progesterone concentrations and vaginal cytology [Sharpe et al., 1990a; Sharpe et al., 1990b]. Of rats receiving Antide plus either estrogen, estrogen plus progesterone, progesterone alone or no steroid add-back thereby, only the uteri of rats receiving progesterone synthesized and secreted PUP-1 into the uterine culture medium. Furthermore, the progesterone-induced synthesis and secretion of PUP-1 is blocked by administration of Onapristone, a progesterone antagonist (ZK 98.299; Schering AG, Berlin, Germany) [Sharpe and Zimmer, 1993]. Following three days of treatment, Onapristone suppressed the progesterone stimulated synthesis and secretion of PUP-1 in a dose related fashion without altering uterine weight. At equal doses of Onapristone and progesterone, serum progesterone was elevated yet PUP-1 synthesis and secretion remained suppressed. These data suggest the inhibitory action of Onapristone on PUP-1 protein production was most likely due to a direct effect on the endometrium. Applicants have also observed that medroxyprogesterone acetate (MPA) enchances rat and human endometrial stromal cell PUP-1 synthesis and secretion in vitro. These studies indicate that endometrial protein production, in particular PUP-1 synthesis and secretion, is modulated by agents that alter steroid production. Agents used for ovarian hyperstimulation/ovulation induction (including GnRH analogues as shown above) in women may also alter endometrial protein production and be deleterious to the process of implantation. Yet, to date no marker to monitor the effects of ovarian hyperstimulation/ovulation induction on uterine receptivity is presently available. The present invention provides a method for monitoring the effects of such induction stimulation on uterine receptivity.

The present invention also provides a method for female contraception by disrupting the cyclic presence of PUP-1. The interruption can be to reduce or eliminate PUP-1 presence during the uterine receptivity window for implantation of the menstral cycle.

The disruption can be induced by an antagonist of PUP-1. The term antagonist or antagonizing is used in its broadest sense. Antagonism can include any mechanism or treatment which results in inhibition, inactivation, blocking or reduction in PUP-1. For example, the antagonizing step can include blocking cellular receptors for PUP-1 or can be by administering Onapristone, a progesterone antagonist (ZK 98.299; Schering AG, Berlin, Germany) as is known in the art. Additionally other antagonists such as TIMP-1 (tissue inhibitor of metalloproteinases-1) and other antagonists of MMP can be utilized in the method of the present invention [Hodgson, 1995; Gordon et al, 1993; Lagrenie et al, 1996].

The antagonist compounds utilized in the present invention, are administered in combination with other drugs or singly consistent with good medical practice. The composition is administered and dosed in accordance with good medical practice taking into account the clinical condition of the individual patient, the site and method of administration, scheduling of administration, and other factors known to medical practitioners. The "effective amount" for purposes herein is thus determined by such considerations as are known in the art. Practitioners of ordinary skill in the art can readily determine optimum dosages, dosing methodologies, and repetition rates. The amount must be effective to interrupt the cyclic presence of PUP-1.

In general the antagonist is administered during the period of the menstrual cycle when there is uterine receptivity. The antagonist can be administered by application to a diaphragm, vaginal suppository, and douche before or after coitus to block pre-embryo implantation. U.S. Pat. Nos. 4,564,362 and 4,922,928 incorporated herein by reference in their entirety provide examples of delivery methods for contraceptive agents.

The above discussion provides a factual basis for the use of PUP-1 glycoprotein and functional analogs. The methods used with and the utility of the present invention can be shown by the following examples.

EXAMPLES

General Methods

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series, Vols.* 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). Insitu (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described were generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Example 1

Isolation and Characterization of Glycoprotein

Materials and Methods
Endometrial Tissue

Human tissues were obtained from randomly selected, informed volunteer patients routinely presenting to the physicians in the Department of Obstetrics and Gynecology at the University of Missouri Medical School as approved by the Institutional Review Board. Patients presented for a variety of routine diagnostic and therapeutic examinations including diagnosis of endometrial function, endometriosis, tubal ligation for sterilization, routine gynecological care and gamete intrafallopian transfer.

Endometrial tissue was obtained using a Pipelle™ (Unimar, Wilton, Conn.) endometrial suction curette. The date of the patients last menstrual period and use of any medication were also recorded. Endometrial tissues were classified as proliferative (days 4 to 14) or secretory (days 15 to 28) according to the date of their last menstrual period. Endometrial dating was confirmed by histological evaluation by the Pathology Department at the University of Missouri. Tissue specimens were transported to the laboratory in saline and, using a dissecting microscope, dissected free of adnexa. Epithelial and stromal cell cultures plus tissue explant cultures were processed as described below.
Epithelial and Stromal Cell Isolation And Purification Epithelial and stromal cells were obtained by enzymatic dissociation and a series of filtrations and sedimentations according to the protocol of Osteen et al. [1989] with modifications described by Sharpe et al. [1992].

Briefly, cells were enzymatically dissociated from endometrial and endometriotic tissues during a 1 hour incubation in phenol-red free Dulbecco's Modified Eagle's Medium/Ham's F-12 (DMEM/Ham's F-12; Sigma Chemical Co., St. Louis, Mo.) containing 0.5% collagenase (Clostridium histolyticum, catalogue number 840-7018IH), 0.02% deoxyribonuclease (DNase, Sigma Chemical Co., St. Louis, Mo.) and 2% horse serum (Vector Laboratories, Burlingame, Calif.) in a shaking incubator at 37° C. After 1 hour, the solutions containing the dissociated cells were filtered through an 88 $\mu$m nylon mesh filter. The stromal cell fractions that passed through the 88 $\mu$m filter were further purified by gravity sedimentation and a final filtration through a 37 $\mu$m nylon mesh to remove remaining epithelial cells. Cell viability (0.04% trypan blue exclusion test) and number (Makler Counting Chamber, T.S. Scientific, Perkasie, Pa.) were evaluated in aliquots of the cells.

The epithelial cell fractions retained by the filters in the initial filtration step were subjected to a second enzymatic digestion for 30 to 45 minutes or until cell clumps were dispersed. The dispersed epithelial cell fractions were further purified by gravity sedimentation and selective attachment procedures [Sharpe et al., 1992]. Cell number and viability were evaluated as described for the stromal cell fractions.

Isolation and purification of epithelial and stromal cells yielded an average of $2.1 \times 10^4$ viable epithelial cells and $2.6 \times 10^5$ viable stromal cells per mg of tissue. Both stromal and epithelial cell fractions were diluted to a density of $1 \times 10^6$ viable cells/mL. Stromal cell suspensions (0.8 ml each) were plated in plastic organ culture dishes (Falcon 3037, Falcon Plastics, Oxnard, Calif.) for a total of $8 \times 10^5$ viable cells in a surface area of 176.25 mm$^2$. Epithelial cell suspensions (0.4 ml) were plated in Millicelle CM culture inserts (Millipore, Bedford, Mass.) coated with 0.2 ml of the extracellular matrix Matrigel (non-diluted; Collaborative Research Inc., Bedford, Mass.) providing a total of $4 \times 10^5$ viable cells in a surface area of 78.50 mm$^2$. Aliquots of the epithelial cell suspensions were also plated on plastic cultureware for immunocytochemical analysis as Matrigel® often created an unacceptable background in the staining process. Other than the elimination of the high background staining, the results of the immunostaining did not vary between the two culture types (matrix vs plastic).

All cultures were kept in a humidified incubator at 37° C. with 5% $CO_2$. Culture media consisted of phenol-red free DMEM/Ham's F-12 containing 10% heat-inactivated fetal bovine sera (GIBCO/BRL, Grand Island, N.Y.) for the first 6 days of culture. By day 8 of culture, the cells had achieved approximately 95% confluence and protein studies were initiated. The cultures were rinsed three times with phosphate buffered saline and the media was replaced with serum-free minimal essential medium (MEM; Gibco/BRL, Grand Island, N.Y.) containing L-[$^{35}$S] methionine (20 $\mu$Ci/mL; Du Pont New England Nuclear, Boston, Mass.) for 24 hours. Incubations were terminated by centrifugation of the media at 3000×RPM for 15 minutes at 4° C. Media containing the de novo synthesized proteins were dialyzed ($M_r$ cut off 6-8000) against 1.0 mM tris (hydroxymethyl) aminomethane HCl, pH 8.2 at 40° C. and lyophilized.

Cell morphology was assessed and photomicrographed at plating (day 0) and days 4, 6, 8 and 12 at ×100, ×200 and ×400 magnification using a Nikon Diaphon™ inverted phase contrast microscope (Nikon, Inc., Garden City, N.Y.) with a Hoffman Modulation Contrast System (Modulation Optics, Inc. Greenvale, N.Y.). Cells were evaluated before and after immunostaining and with a hematoxylin counterstain.

A variety of intermediate filament protein, glycoprotein and secretory protein markers were used to assess the various cell types present in the endometrial and endometriotic cell cultures. Attempts were made to identify a marker which would distinguish between endometriotic cells and peritoneal cells. Murine monoclonal antibodies (MAbs) against: cytokeratins 8, 18 and 19 (for epithelial cells; Biodesign clone NCL-5D3; Kennebunkport, Me.); vimentin (for stromal cells; Boehringer Mannheim clone V9; Indianapolis, Ind.); a human epithelial cell marker directed against a 200 kilo-Dalton glycoprotein, BMA 180 (also known as BW 495/36; for endometrial epithelial cells; Behringwerke AG, Marburg, Germany); and for pregnancy-associated endometrial $\alpha_2$-globulin ($\alpha_2$-PEG; C6H11; for secretory phase endometrial epithelial cells) were used to assess the cells at plating and on days 4, 6, 8 and 12. The $\alpha_2$-PEG (C6H11; 1:100) MAb used as a marker of secretory phase epithelial cell purification and also as an indicator of physiological function in vitro by Western blot analysis of explant culture media separated by 2D-PAGE. Single and double labeling immunocytochemical techniques were performed using the Vectastain® ABC (avidin:biotin complex peroxidase procedure) and ABC-AP (avidin:biotin complex alkaline phosphatase procedure) Kits (Vector Laboratories) as per manufacturer's instructions. Peroxidase activity was demonstrated by incubation with 3,3'-diaminobenzidine substrate yielding a brown intracellular precipitate which confirmed peroxidase staining. Alkaline phosphatase activity was demonstrated with the Vectastain® Alkaline Phosphatase Substrate Kit I—Vector Red yielding a pinkish-red stain which confirmed alkaline phosphatase activity. Cells were counterstained with hematoxylin. Cells incubated with phosphate buffered saline substituted in place of primary antibody were included as negative controls in all immunostaining procedures. Using inverted phase contrast microscopy, multiple fields (×200) per cell type were evaluated for the percent of reactive cells.

Tissue Explant Culture:

As controls for the isolated epithelial and stromal cell fractions, endometrial tissue explants (approximately 100 mg wet weight) were incubated in MEM in the presence of L-[$^{35}$S] methionine (20 $\mu$Ci/ml) as previously used by Sharpe et al. [Sharpe et al., 1991] and Sharpe and Vernon [Sharpe and Vernon, 1993]. Within 30 minutes of collection, tissue explants were cultured for 24 hours at 37° C. on a rocking platform (6 cycles per minute) in a gaseous atmosphere of 50% nitrogen, 45% oxygen and 5% carbon dioxide. Tissue explant culture media were harvested and processed for protein analysis as described above for cell culture media.

Two-Dimensional Electrophoresis and Western Blot Analysis:

Two-dimensional polyacrylamide gel electrophoresis (2-D SDS-PAGE) was performed as previously employed by Sharpe et al. [1993] and Sharpe and Vernon [1993]. To evaluate the de novo synthesized radiolabeled proteins, aliquots of lyophilized cell culture and tissue explant media containing $1.5 \times 10^6$ non-dialyzable cpm (6,000 to 8,000 $M_r$ cutoff) were applied to the first dimension isoelectric focusing gels. Molecular weight markers (Pharmacia LKB Biotechnology, Inc. Piscataway, N.J.) were added to the polyacrylamide (12%) second dimension slab gels. Proteins separated by two dimensional SDS-PAGE were transferred to nitrocellulose membranes (Schleicher and Schuell, Keene, N.H.) at one amp constant current for one hour using the Hoeffer Transphor® Blot System (Hoeffer Scientific, San Francisco, Calif.) and visualized by fluorography. The BioRad 2D Analyst software with BioRad Model 620 densitometer was used to create digital contour maps of images on the fluorographs made from the two-dimensional SDS-PAGE protein separations. Computer generated peak reports were used for qualitative comparison of proteins from the contour maps. Due to the overload of protein in some of the two-dimensional SDS-PAGE gels and possible loss of resolution following transfer of the proteins to nitrocellulose prior to autoradiography, only protein groups representing at least 10% of the integrated intensity were evaluated. Quantitative comparisons between patients or between tissue/cell cultures were not made.

Results

Endometrial Tissue Specimens

Twenty-nine specimens were evaluated (Table 1). Twenty-two of the specimens were obtained from women with histories of regular menses. Seven additional specimens were obtained from women with atypical or absent menstrual cycles. Specimens ranged from 29 mg to over 4 g in weight. Up to 100 mg of tissue was used for explant culture and remaining tissue was enzymatically dissociated for the cell culture experiments.

Protein Synthesis and Secretion

Figure 2A:
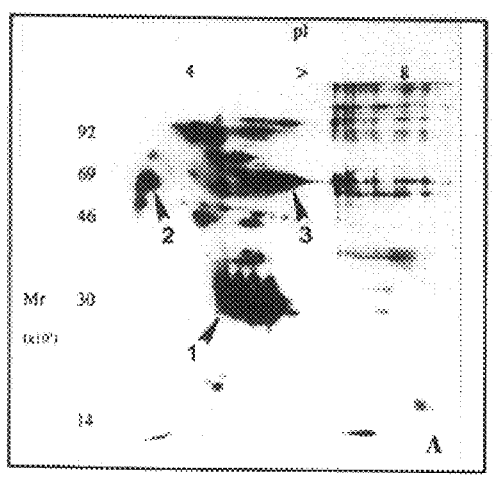
FIGS. 2A–2B are photographs of representative two dimensional SDS-PAGE fluoragraphs of L-[$^{35}$S] methionine-labeled secretory proteins from secretory phase endometrial epithelial cell FIG. 2(A), and endometriotic FIG. 2(B) explant culture media.
Figure 2B:
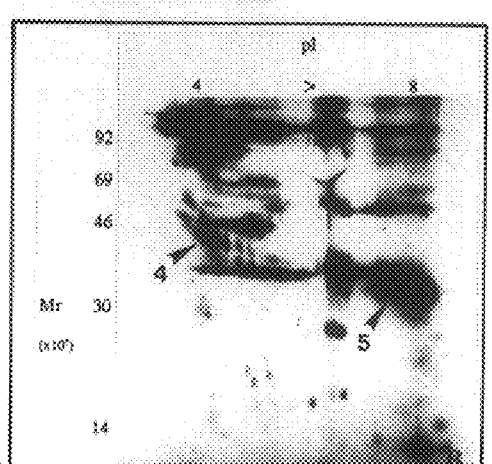

Patterns of proteins synthesis and secretion made from the isolated endometrial epithelial and stromal cell culture media from women with regular menses were studied (FIGS. 1A–D). Of the hundreds of proteins visualized on the two-dimensional SDS-PAGE fluorographs, PUP-1 ($M_r$ 70,000; pI 5.7) was synthesized and secreted by secretory, but not proliferative phase, endometrial stromal cells. The patterns of synthesis and secretion of the proteins visualized and evaluated in the cell culture media were identical to those evaluated in the explant culture media (FIGS. 2A–B). PUP-1 was produced by secretory phase endometrial explant tissues but not by proliferative phase (non-receptive) tissue explants.

A limited number of specimens were cultured from women reporting atypical or absent menses. Proliferative endometrium from a patient with irregular uterine bleeding (no current medication) aberrantly synthesized and secreted PUP-1. This was the only case in which PUP-1 was produced by a proliferative endometrial specimen. Subsequent histological diagnosis revealed adenomyosis.

Epithelial and Stromal Cell Culture

Figure 3A:
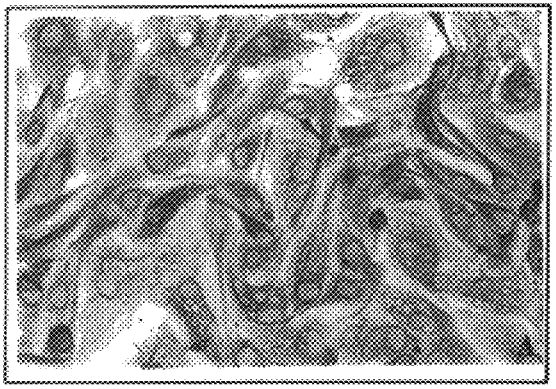
FIGS. 3A–3F are photomicrographs of primary cultures of separated epithelial and stromal cells from endometrial and endometriotic biopsy specimens wherein FIG. 3(A) endometrial epithelial cell culture, day 8, cytokeratin mAb (×400)
Figure 3B:
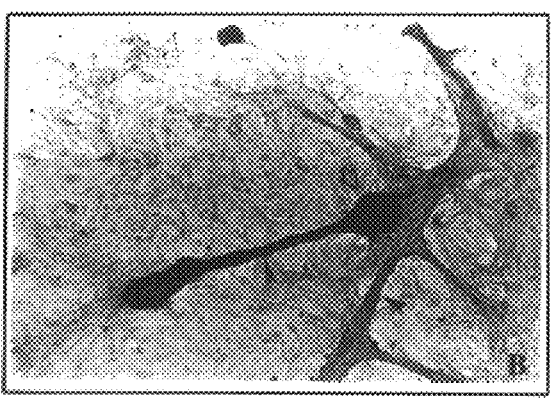
Figure 3C:
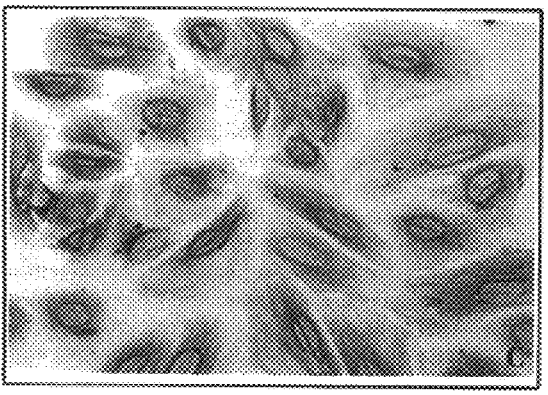
Figure 3D:
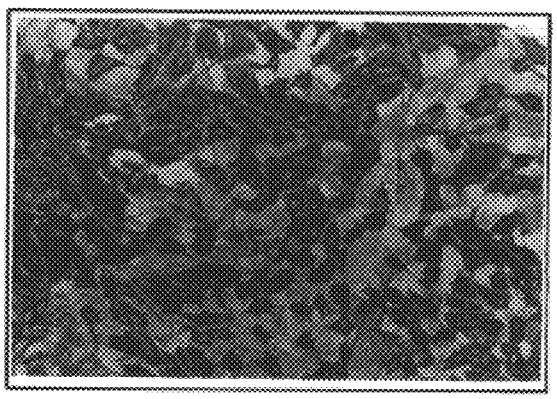
Figure 3E:
Figure 3F:
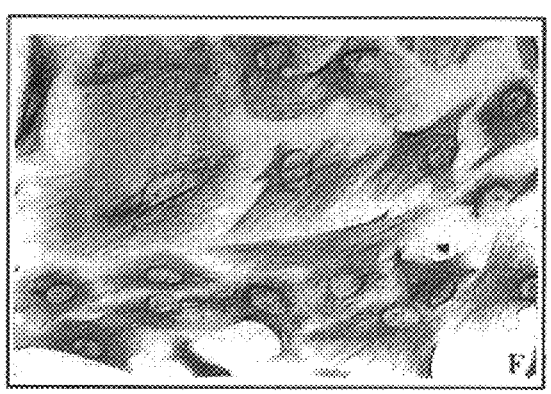

Morphologically, by day 8 of culture, endometrial epithelial cells cultured on the extracellular matrices plated on a semipermeable membrane appeared as homogeneous populations of tadpole-shaped cells with prominent, off-centered nuclei and whorling cell-cell processes that wrapped around adjacent cells (FIG. 3A). By day 12 of culture, the monolayers of endometrial epithelial cells formed three-dimensional mounds of cells which appeared interconnected by tubular processes resembling glandular-like structures (FIG. 3B). Endometrial stromal cells displayed a homologous, cobblestone mosaic-like, single cell monolayer pattern. The endometrial stromal cells had centrally located nuclei, distinct cytoplasmic borders which did not overlap and did not demonstrate cell-cell processes throughout the experiment (FIG. 3C).

The results of the immunocytochemical staining of the cells did not differ between the day of plating and days 4, 6, 8 and 12 and are presented in Table 2. Endometrial epithelial cells, especially those cells involved in formation of the epithelial cell mounds and tubular gland-like structures, displayed strong immunoreactivity with the cytokeratin and BMA 180 MAbs. Few (<3%) of the cells in the endometrial epithelial cells were decorated with the vimentin MAb suggesting limited stromal cell contamination of the epithelial cell cultures. Secretory, but not proliferative phase, endometrial epithelial cells were also decorated with the $\alpha_2$-PEG MAb (C6H11).

Endometrial stromal cells were decorated with the vimentin MAb and did not display immunoreactivity with the epithelial cell markers BMA 180 and $\alpha_2$-PEG.

Example 1 shows an unique, endometrial secretory protein which is useful in the development of novel diagnostic, prognostic and therapeutic methods for the management of endometrial receptivity. Furthermore, understanding biochemical differences associated with endometrium enhances our knowledge of endometrial receptivity providing for new treatment approaches related to reproductive dysfunction and contraception.

PUP-1 is a major product of secretory, but not proliferative, endometrial explant and stromal cell cultures. PUP-1 is also found in a proliferative phase endometrial explant culture derived from a patient who was taking MPA for irregular uterine bleeding. These observations suggests that PUP-1 is P modulated and may play a role in progesterone-dependent uterine function.

Example 2

Immunolocalization of PUP-1 In Human Endometrium, and Endometrial Epithelial and Stromal Cell Cultures Materials and Methods Supplies:

Pipelle™ endometrial suction curettes were obtained from Unimar (Wilton, Conn.). 10% neutral buffered formalin was purchased from Fisher Scientific (St. Louis, Mo.). Millicelle CM culture inserts were obtained from Millipore (Bedford, Mass.) and plastic organ culture dishes (Falcon 3037) were purchased from Falcon Plastics (Oxnard, Calif.). Matrigel® was purchased from Collaborative Research Inc. (Bedford, Mass.). Dulbecco's Modified Eagle's Medium/ Ham's F12 (DMEM/Ham's F-12) and 10 % heat-inactivated fetal bovine sera (FBS) were obtained from GIBCO/BRL (Grand Island, N.Y.). Immunochemical supplies including the Vectastain ABC Kits and 3,3'-diaminobenzidine substrate were purchased from Vector Laboratories (Burlingame, Calif.). Murine monoclonal antibodies were obtained as follows: cytokeratins 8, 18 and 19 (Biodesign clone NCL-5D3; Kennebunkport, Me.); vimentin (Boehringer Mannheim clone V9; Indianapolis, Ind.); a human epithelial cell marker directed against a 200 kilo-Dalton glycoprotein, BMA 180 (Behringwerke AG, Marburg, Germany); pregnancy-associated endometrial $\alpha_2$-globulin ($\alpha_2$-PEG; C6H11, a generous gift from Stephen C. Bell, Ph.D., Departments of Obstetrics and Gynecology and Biochemistry, University of Leicester, Leicester, United Kingdom). Chromatography supplies were purchased as follows: Affi-Gel blue affinity gel, BioRad Laboratories (Melville, N.Y.) and wheat germ lectin sepharose 6MB, Pharmacia Biotech Inc. (Piscataway, N.J.). Nitrocellulose membranes were purchased from Schleicher and Schuell (Keene, N.H.). The Hoeffer Transphor® Blot System was purchased from Hoeffer Scientific (San Francisco, Calif.).

Endometrial Tissues

Human endometrial tissues were used for immunohistochemical localization of PUP-1 and as a source of endometrial epithelial and stromal cells. Tissues were obtained from informed volunteer patients routinely presenting to the physicians in the Department of Obstetrics and Gynecology at the University of Missouri Medical School as approved by the Institutional Review Board using a Pipelle™ endometrial suction curette. The date of the patient's last menstrual period and use of any medication were recorded. Endometrial tissues (n=30) were classified as proliferative (days 4 to 14) or secretory (days 15 to 28) according to the date of their last menstrual period. Endometrial dating was confirmed by histological evaluation by the Pathology Department at the University of Missouri.

Tissue specimens were transported to the laboratory in saline. In the laboratory, a representative portion of each endometrial biopsy was fixed in 10% neutral buffered formalin while remaining tissue was enzymatically dissociated to obtain endometrial stromal cells.

Endometrial Cell Isolation, Purification and Culture

Endometrial epithelial and stromal cells were used for immunocytochemical localization of PUP-1 and as a source of PUP-1 for antibody production. Cells were isolated and purified by enzymatic dissociation and a series of filtrations and sedimentations according to the protocol of [Osteen et al., 1989] with modifications previously described by [Sharpe et al., 1993]. Epithelial and stromal cells were diluted with culture media to a final concentration of $1.0 \times 10^6$ viable cells/ml. Epithelial cell suspensions (0.4 ml) were plated in Millicelle CM culture inserts coated with 0.2 mL of the extracellular matrix Matrigel® (non-diluted) providing a total of $4 \times 10^5$ viable cells in a surface area of 78.50 mm$^2$. Aliquots of the epithelial cell suspensions were also plated on plastic cultureware as Matrigel® created an unacceptable background in the immunocytochemical staining process. Other than the elimination of the high background staining, the results of the immunostaining did not vary between the two culture types (matrix vs plastic). Stromal cell suspensions (0.8 ml each) were plated in plastic organ culture dishes for a total of $8 \times 10^5$ viable cells in a surface area of 176.25 mm$^2$. All cultures were kept in a humidified incubator at 37° C. with 5% $CO_2$. Culture media consisted of phenol-red free DMEM/Ham's F-12 containing 10% heat-inactivated FBS for the first 3 days of culture. By day 4 of culture, the cells had achieved approximately 95% confluence and immunocytochemical studies were performed.

The purity of the cell cultures was immunocytochemically assessed using a variety of intermediate filament protein, glycoprotein and secretory protein markers as previously described by Sharpe et al. [Sharpe et al., 1993]. Antibodies (MAbs) against cytokeratins (for epithelial cells), vimentin (for stromal cells); a human epithelial cell marker directed against a 200 kilo-Dalton glycoprotein, BMA 180 (for endometrial epithelial cells, and for pregnancy-associated endometrial $\alpha_2$-globulin ($\alpha_2$-PEG; for secretory phase endometrial epithelial cells) were used to assess the cells using the Vectastain® ABC Kit as per manufacturer's instructions. Peroxidase activity was demonstrated by incubation with 3,3'-diaminobenzidine substrate yielding a brown intracellular precipitate which confirmed peroxidase staining. Cells were counterstained with hematoxylin. Preimmune rabbit sera substituted in place of primary antibody was used as a negative control in all immunostaining procedures.

Generation of PUP-1 Ab from Partially Purified PUP-1

For the generation of the PUP-1 antibody, de novo synthesized PUP-1 was partially purified from human endometrial stromal cell culture media. The stromal cells were isolated from a biopsy collected at cycle day 19. The biopsy which weighed 159 mg (wet weight) yielded $7 \times 10^6$ epithelial cells which were >90% viable and $42 \times 10^6$ stromal cells which were >80% viable.

Partial purification was achieved by passing the cell culture media containing the de novo synthesized PUP-1 over Affi-Gel blue affinity gel and wheat germ lectin sepharose 6MB. Affi-Gel blue affinity gel was used to remove "contaminating" serum albumin. The wheat germ lectin sepharose, which "sees" certain N-acetylglucosamine and terminal sialic acid residues, bound PUP-1 and other glycosylated proteins to the column matrix. PUP-1 was subsequently eluted with hapten (N-acetylglucosamine). The partially purified proteins isolated by the chromatographic procedures, including PUP-1, were further separated by two dimensional sodium dodecyl sulphate polyacrylamide gel electrophoresis (2D-SDS-PAGE) and then transferred to nitrocellulose membranes at one amp constant current for one hour using the Hoeffer Transphor® Blot System. Proteins transferred to the membranes were visualized by India ink staining. The stained protein "spot" which corresponded to the molecular weight and isoelectric point of PUP-1 ($M_r$ 70,000; pI 5.7) was cut from several nitrocellulose membranes and used as immunogen [Knudsen K A, 1985].

Polyclonal anti-PUP-1 was synthesized "off blot" using a male New Zealand White rabbit and a golf ball-induced granuloma technique [Hillam et al., 1974]. Prior to immunization, ascites fluid was collected for use as a negative control in the immunostaining procedures. An initial immunization of approximately 500 $\mu$g and two subsequent booster immunizations of approximately 250 $\mu$g each of PUP-1 antigen were administered. Immunoreactivity and specificity of the PUP-1 antibody was tested two weeks after each immunization by Western blot analysis of 2D-SDS-PAGE separations of endometrial stromal cell culture media.

Immunochemical Staining for PUP-1

Endometrial tissues were formalin fixed, routinely processed, paraffin embedded and sectioned at 3 $\mu$m. After dewaxing, sections were hydrated and equilibrated with phosphate buffered saline (PBS). Endogenous peroxidase activity was quenched by treatment with 3% hydrogen peroxide. Immunohistochemical staining was performed with the PUP-1 antibody (1:500) using the Vectastain® ABC kit according to manufacturer's instructions. Peroxidase activity was demonstrated by incubation with 3,3'-diaminobenzidine substrate yielding a brown intracellular precipitate which confirmed peroxidase staining. Sections were then counterstained with hematoxylin. Tissue sections were also incubated with preimmune ascites fluid or phosphate buffered saline substituted in place of primary antibody as negative controls for the immunostaining procedures. No immunostaining was seen in any of these controls which served as the negative staining standard. Photomicrographs were made for documentation.

Near confluent epithelial and stromal cell cultures were immunocytochemically stained for PUP-1 (1:500) using the Vectastain® ABC procedure as described above. Morphometric analysis was used to analyze the proportion of cells exhibiting PUP-1 staining [Weibel E R, 1979]. PUP-1 staining was evaluated in multiple high power fields (400×) of each cell culture. Cells with a brown cytoplasmic precipitate were considered to have stained positive for PUP-1. The proportion (%) of cells exhibiting positive PUP-1 staining was calculated by dividing the number of positively stained cells by the total number of cells counted. Student's t-test was used to confirm statistical significance of staining scores between the proliferative and secretory stages of the menstrual cycle.

Results

Endometrial Tissue Specimens

Thirty specimens were obtained from women with histories of regular menses. The specimens ranged from 29 mg to 250 mg in weight. Additional specimens obtained from women with atypical or absent menstrual cycles were not included in the study.

Endometrial Epithelial and Stromal Cell Isolation and Purification

Endometrial epithelial cells cultured on the extracellular matrices plated on a semipermeable membrane appeared as homogeneous populations of tadpole-shaped cells with prominent, off-centered nuclei and whorling cell-cell processes that wrapped around adjacent cells. Morphometric analysis of the homogeneity of the endometrial epithelial cell cultures revealed that 95–98% of the epithelial cells were decorated with cytokeratin and BMA 180 antibodies; 98% of the secretory stage epithelial cells (but not the proliferative stage epithelial cells) stained with the $\alpha_2$-PEG antibody; and less than 5% of the endometrial epithelial cells stained with the vimentin antibody suggesting limited stromal cell contamination of the epithelial cell cultures.

The endometrial stromal cells displayed a cobblestone mosaic-like, monolayer pattern with distinct cytoplasmic borders which did not overlap and did not demonstrate cell-cell processes. Polygonal-shaped cells with centrally located nuclei were the most numerous in the stromal cell cultures (82%) but elongated spindle-shaped cells with centrally located nuclei and large amounts of cytoplasm (12%) and rounded cells with large nuclei and sparse cytoplasm (3%) were also present. Despite the polymorphic morphology, $\geq 98\%$ of the cells in the stromal cell cultures were decorated with the vimentin antibody but $\leq 2\%$ were decorated with the cytokeratin, BMA 180 or $\alpha_2$-PEG antibodies suggesting limited epithelial cell contamination of the stromal cell cultures.

PUP-1 Purification and Antibody Production

Sufficient PUP-1 antigen was obtained from the cycle day 19 endometrial biopsy stromal cell culture media for "off-blot" generation of the PUP-1 antibody. Anti-PUP-1 was present in the ascites fluid obtained after the second booster immunization. A third immunization was given to enhance the response. Specificity of the PUP-1 antibody was determined using Western blot analysis of 2D-SDS-PAGE separated endometrial epithelial and stromal cell culture media. PUP-1 antibody recognized a single protein "spot" corresponding to the molecular size ($M_r$ 70,000) and isoelectric point (pI 5.7) of PUP-1 on the endometrial stromal cell culture media blots. No immunoreactivity was detected on the endometrial epithelial cell culture media blots.

PUP-1 Localization In Human Endometrial Tissues Throughout The Menstrual Cycle

The pattern of PUP-1 immunohistochemical localization (brown intracellular precipitate) in paraffin embedded endometrial tissues varied with the stage of the menstrual cycle. At cycle day 8, PUP-1 was localized in the endometrial stroma, at cycle day 14, PUP-1 was localized in the endometrial stroma and in the apical region of the ciliated luminal epithelium. At cycle day 19, PUP-1 was localized in the endometrial stroma and apical regions of the glandular and luminal epithelium. At cycle day 25, scant PUP-1 was noted in the stroma with reduced PUP-1 staining in glandular and luminal epithelium when viewed at either 200× or 400×. No immunostaining was observed when preimmune sera was substituted in place of PUP-1 antibody. PUP-1 immunoreactive secretory material was also present in the lumina of the endometrium and glandular epithelium during the mid- to late secretory stage of the cycle but was immunonegative for PUP-1 in the controls stained with preimmune sera in place of the PUP-1 antibody.

During the proliferative stage (days 4–12 evaluated), PUP-1 was localized as a brown preciptate in the endometrial stroma. At cycle day 14, coinciding with the time of ovulation, PUP-1 staining was again documented in the endometrial stroma but also noted in the apical region of the ciliated luminal epithelium. During the mid-secretory stage (cycle days 18–22), PUP-1 was localized in the endometrial stroma and apical regions of the glandular and luminal epithelium. Secretory material immunoreactive for PUP-1 was present in the lumina of the endometrium and glandular epithelium during the mid- to late secretory stage of the cycle but was immunonegative for PUP-1 in the controls stained with preimmune sera in place of the PUP-1 antibody. By cycle day 25, only scant PUP-1 was noted in the stroma with reduced PUP-1 staining in glandular and luminal epithelium as compared to the mid-secretory stage of the cycle. No immunostaining was observed when preimmune sera was substituted in place of PUP-1 antibody.

Localization of PUP-1 in Endometrial Cell Cultures

Distinct subpopulations of the isolated, cultured endometrial stromal cells were decorated with the PUP-1 antibody during both the proliferative (mean±SEM 25.7±2.9%) and secretory (24.6±3.7%) stages of the menstrual cycle. PUP-1 staining appeared more intense in the spindle-shaped cells and rounded cells than the polygonal-shaped cells. No immunostaining was noted when preimmune sera was substituted for primary antibody. The stromal cells which stained positively for PUP-1 displayed a diverse morphology including all three types of cells observed in the stromal cell cultures. PUP-1 staining appeared more intense, however, in the rounded and spindle-shaped cells than the polygonal-shaped cells. Endometrial epithelial cells were not decorated with the PUP-1 antibody. No immunostaining was noted when preimmune sera was substituted for primary antibody.

Example 2 demonstrates that the pattern of PUP-1 immunostaining shifts from the endometrial stroma alone during the proliferative stage of the menstrual cycle, to both the endometrial stroma and glands around the time of ovulation and continuing through the mid-secretory stage of the cycle, and eventually dissipates from the endometrium as menses approaches during the late secretory stage of the menstrual cycle. This example also shows that PUP-1 localizes in subpopulations of isolated, cultured endometrial stromal cells but not endometrial epithelial cells.

These observations correlate well with Applicant's previous studies which established that PUP-1 is synthesized and secreted in vitro by cultured endometrial biopsy explants and by isolated endometrial stromal cells, but not epithelial cells, when the tissues are collected during the secretory stage of the menstrual cycle [Sharpe et al., 1993]. Collectively, these observations show that PUP-1 is synthesized by the endometrial stroma and subsequently transferred to the glandular and luminal epithelium for secretion during the secretory stage of the menstrual cycle. The fact that PUP-1 immunostaining was found in proliferative stage endometrial stromal tissues and stromal cells isolated from proliferative stage endometrial biopsies combined with the absence of PUP-1 in proliferative stage endometrial explant or stromal cell culture media further suggests that proliferative stage endometrial stroma may act as a site of storage of PUP-1.

Only distinct subpopulations of the isolated, cultured endometrial stromal cells were decorated with the PUP-1 antibody.

In summary, Example 2 demonstrates that localization of the progesterone-induced uterine protein, PUP-1, in specific cells of the human uterine endometrium is dependent on the stage of the menstrual cycle.

Example 3

The objective of Example 3 was to determine if PUP-1 was present in the decidua and placenta throughout gestation.

Design

Human placental tissues were randomly obtained from first, second and third trimesters of pregnancy.

Materials and Methods

Tissues (n=44) were formalin fixed, paraffin embedded, sectioned at 5 µm and immunohistochemically stained for PUP-1 using the avidin-biotin peroxidase procedure. Tissue sections were also immunohistochemically stained for cytokeratin and prolactin to identify specific cell populations. The patterns of immunostaining were observed by three independent workers.

Results

Syncytiotrophoblast, villous cytotrophoblast and intermediate cytotrophoblast cells were decorated with the cytokeratin antibody but not the prolactin antibody. Decidual cells were decorated with the prolactin antibody but not the cytokeratin antibody and thus could be distinguished from trophoblast cells. Decidual cells and intermediate trophoblast cells exhibited positive PUP-1 immunostaining associated with typical secretory phase endometrial stromal cells. Focal PUP-1 staining was noted in syncytiotrophoblast but not found in endothelium or mesenchyme.

Conclusion

PUP-1, a product of secretory phase endometrial stromal cells, localizes in decidua and trophoblast throughout gestation thereby providing an indication of normal placental physiology.

Example 4

As shown hereinabove, progesterone-induced uterine protein-1, PUP-1, (Mr 70,000; pI 5.7), is synthesized and secreted by rat and human endometrial explants and endometrial stromal cells (but not endometrial epithelial cells) when tissues and cells are collected from either progesterone-treated or reproductively cyclic uteri during periods of elevated serum progesterone [Sharpe et al., 1991; Sharpe et al., 1993b]. Rat endometrial PUP-1 production is also elevated at a time coinciding with the entry of fertilized oocytes into the uterus and peaks around the time of implantation [Sharpe et al., 1993a].

This Example was designed to identify and characterize PUP-1 by sequence analysis and comparison of deduced sequence to data bases to determine homology to known proteins. Using methods detailed herein above, de novo synthesized PUP-1 was partially purified from human endometrial stromal cell culture media using wheat germ lectin sepharose affinity chromatography and two-dimensional SDS-PAGE or alternatively rat tissue. The partially purified protein was electrophoretically transferred to polyvinyl difluoride membranes which were stained with Coomassie Blue R-250. Stained protein corresponding to PUP-1 was cut from the membranes for amino acid sequencing. Partial amino acid sequence was determined by automated Edman degradation using an Applied Biosystems 470Aa gas phase sequencer with an on-line phenylthiohydantoin analyzer.

Results

SEQ ID No:1 is the amino acid sequence of the N-terminal segment of human PUP-1. The bottom sequence (SEQ ID No:2) is that of rat PUP-1.

(SEQ ID No:1) YPLDGAARGEDTSMNLVQKY-LENYYDLXKD (SEQ ID No:2) YPLHRSEEDALTEVLQDYLXNY

When rat PUP-1 N-terminal sequence was compared to rat transin (also called stromelysin-1 and MMP-3) there were four mismatched amino acids comparing the 21 amino acids N-terminal sequence providing 81% homology. The human PUP-1 N-terminal sequence when compared to human stromelysin-1 (also called MMP3) showed 100% sequence homology for the N-terminal segment indicating that PUP-1 appears to be part of the MMP family of proteins.

Example 5

Using Western blot analysis with PUP-1 antisera, Applicants have found PUP-1 is present in culture media and uterine washings from uteri recovered from secretory phase, simulated pregnant and progesterone-treated baboons. Simulated pregnant baboons received 12 days of hCG. On the twelfth day, they received estradiol and progesterone implants. Uteri were flushed starting on the seventh day of hCG treatment and daily until seven days after cessation of hCG treatment.

| | PREGNANCY SIMULATION PROTOCOL | | | | | | | | | | | | | | | | | | |
|---|---|---|---|---|---|---|---|---|---|---|---|---|---|---|---|---|---|---|---|
| Days | 1 | 2 | 3 | 4 | 5 | 6 | 7 | 8 | 9 | 10 | 11 | 12 | 13 | 14 | 15 | 16 | 17 | 18 | 19 |
| hCG | — | — | — | — | — | — | — | — | — | — | — | — | | | | | | | |
| E + P | | | | | | | | | | | | | | | | | | | |
| Serum P (ng/ml) | | | | | | | 6.7 | | 8.2 | | | 6.4 | | 8.9 | | | 9.0 | | |
| Uterine Flush | | | | | | | — | — | — | — | — | — | — | — | — | — | — | — | — |

This protocol elicited serum steroid levels similar to those found in early pregnancy in the baboon. Using Western blot analysis, the PUP-1 antibody recognized a single band migrating to 58–61 kD. Synthesis and secretion of PUP-1 was elevated in the luteal phase, simulated pregnant and progesterone-treated baboons. The detection of PUP-1 in uterine washings is the evidence that PUP-1 is produced in vivo and not just an artifact of in vitro culture.

Applicants have also found human endometrium, like rat and baboon, also synthesizes and secretes PUP-1 in response to progesterone stimulation [Sharpe et al., 1993]. PUP-1 was identified in culture media of human endometrial explants and in culture media of human endometrial stromal cells but not endometrial epithelial cells when tissues were collected during periods of elevated serum progesterone. This study also documented concurrent progesterone-induced synthesis and secretion of the β-lactoglobulin homologue called $\alpha_2$ pregnancy-associated globulin ($\alpha_2$-PEG; also called placental protein 14 or PP 14). While PUP-1 was produced by the endometrial stromal cells, Applicants confirmed the work of others showing that $\alpha_2$-PEG was a product of endometrial epithelial cells [Bell, 1986]. These observations lend validity to Applicants model and support Applicants observation that PUP-1 is a progesterone-induced product of endometrial stromal cells.

In the human, Applicants have demonstrated a shift in the pattern of endometrial PUP-1 immunolocalization from the stroma during the proliferative stage to the stroma and glands during the early to mid-secretory stage of the menstrual cycle coinciding with the time of ovulation, fertilization, embryo cleavage and transport through the oviduct and implantation. PUP-1 immunoreactivity was also observed in the lumina of the epithelial glands. PUP-1 dissipates from the nonpregnant, late-secretory endometrium yet persists and localizes in decidua and trophoblast during gestation. Collectively, these observations show that endometrial PUP-1 plays an autocrine role in the process of endometrial differentiation and decidualizaiton and/or a paracrine role to communicate between the endometrium and the preimplantation embryo and will be useful as a marker of uterine receptivity and blastocyst implantation.

In view of the above experimental data, it must be concluded that there is herein identified a progesterone-induced, estradiol, inhibited uterine protein and functional equivalences, analogs, thereof. The glycoprotein has been identified in cultured media of isolated and purified endometrial stromal cells but not epithelial cells from human tissues. Generally, there is clearly a role for the use of the glycoprotein in the reproductive process and in the clinical evaluation of endometrial function, differentiation and implantation and contraception. Specifically, the glycoprotein and the isolated and purified antibody therefore can be used in the above-described methods of determining endometrial receptivity, reproductive.

Throughout this application various publications are referenced by citation and patents by number. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

| Tissue Source | No. of specimens |
|---|---|
| Source of Tissue Specimens | |
| Regular menses | |
| Matched endometrial/endometriosis biopsy | 16 |
| Endometrial biopsy only | 2 |
| Endometriosis biopsy only | 4 |
| Total | 22 |
| Atypical of absent menses | |
| Endometrial biopsy, irregular bleeding | 1 |
| Endometrial biopsy, irregular bleeding-MPA | 1 |
| Endometrial biopsy, perimenopausal | 1 |
| Endometriosis biopsy, danazol | 2 |
| Endometriosis biopsy; prior hysterectomy | 2 |
| Total | 7 |

TABLE 2

Immunocytochemical Staining of Isolated Populations of Endometrial and Endometriotic Epithelial and Stromal Cell Fractions

| | Epithelial cell fraction | | | Stromal cell fraction | |
|---|---|---|---|---|---|
| | Endometrial tissue | Endometriotic tissue | | Endometrial tissue | Endometriotic tissue |
| | Tadpole | Tadpole | Polymorph | Cobblestone | Cobblestone |
| Cytokeratin | +* | + | + | o | + |
| Vimentin | o† | o | + | + | + |
| BMA 180 | + | + | o | o | o |
| $\alpha_2$-PEG | s‡ | o | o | o | o |

*+, Immunoreactivity detected during proliferative and secretory phases of the menstrual cycle.

TABLE 2-continued

Immunocytochemical Staining of Isolated Populations of Endometrial and Endometriotic Epithelial and Stromal Cell Fractions

| Epithelial cell fraction | | | Stromal cell fraction | |
|---|---|---|---|---|
| Endometrial tissue | Endometriotic tissue | | Endometrial tissue | Endometriotic tissue |
| Tadpole | Tadpole | Polymorph | Cobblestone | Cobblestone |

†o, no immunoreactivity detected in either phase of the menstrual cycle.
‡s, immunoreactivity detected only in secretory phase of the menstrual cycle.

REFERENCES

Angell et al, "Chromosome abnormalities in human embryos after in vitro fertilization" Nature, 303:336 (1987).

Arthur et al, "Variations in concentrations of the major endometrial secretory proteins (placental protein 14 and insulin-like growth factor bind protein-1) in assisted conception cycles" Human Reprod, 10:664–7 (1995).

Barkai et al, "Inhibition of decidual reaction in rats by Clomiphene and tamoxifen" Biol Reprod, 46:733–9 (1992).

Beier, "Uteroglobin-hormone sensitive endometrial protein involved in blastocyst development" Biochim Biophys Acta, 160:289 (1968).

Birkehal-Hansen et al, "Matrix metalloproteinases: a review" Critical Reviews in Oral Biol, 4:197–250 (1993).

Chamberlin and Menino, "Partial characterization of gelatinases produced by preimplantation porcine embryos" Biol Reprod, 52:179, Abstract 492 (1995).

Cohen, "The efficiency and efficacy of IVF and GIFT", Human Reprod, 6:613–18 (1991).

Collier et al, "Platelet activating factor (PAF) production by mouse embryos in-vitro and its effects on embryonic metabolism" J Cell Biochem, 40:387 (1989).

Cornillie et al, "Expression of endometrial protein PP14 in pelvic and ovarian endometriotic implants". Hum Reprod 1991; 6:1141–1415.

Critchley et al, "Role of the ovary in the synthesis of placental protein-14". J Clin Endocrinol Metab 1992; 75:97–100.

Daly et al, Prolactin production during in vitro decidualization of proliferative endometrium. 1983; Am J Obstet Gynecol 145:672–8.

Edwards, "Normal and abnormal implantation in the human uterus" in Implantation of the Human Embryo, Academic Press, Inc. London, 1:303–12, (1985).

Fazleabas et al, "Effect of clomiphene citrate on the synthesis and release of the human β-lactoglobulin homologue, pregnancy associated endometrial $\alpha_2$-globulin, by the uterine endometrium" Human Reprod, 6:783–90 (1991).

Fossum et al, "Ovarian hyperstimulation inhibits embryo implantation in the mouse" J In Vitro Fertil Embryo Trans, 6:7–10 (1989).

Giudice, "Growth factors and growth modulators in human uterine endometrium: their potential relevance to reproductive medicine" Fertil Steril, 61:1–17 (1994).

Godkin et al, "Ovine trophoblast protein 1, an early secreted blastocyst protein, binds specifically to uterine endometrium and affects protein synthesis" Endocrinology, 114:120–30 (1984).

Gordon et al, Metalloproteinase inhibitors as therapeutics, Clin. Exper. Rheumatology 1993; 11(suppl 8): S91–94.

Hampton and Salamonsen, "Expression of messenger ribonucleic acid encoding matrix metalloproteinases and their tissue inhibitors is related to menstruation" J Endocrin, 141:R1–R3, (1994).

Hillam et al. Local antibody production against the murine toxin of Yersinia pestis in a golf ball-induced granuloma. 1974; Infect Immun 10:458–463.

Hodgson, Remodeling MMP's. Matrix metalloproteinase inhibitors will be approved as drugs, probably this year, but questions remain concerning their specificity, bioavailablity and potential long-term toxicity. Biotechnology 1995; 13:554–7.

Jones et al, "Pathophysiology of reproductive failure after clomiphene-induced ovulation", Am J Obstet Gynecol, 108:847–67 (1970).

Joshi et al. Detection and synthesis of a progestagen-dependent protein in human endometrium. J Reprod Fertil 1980; 59:273–85.

Joshi, "Progestin-dependent human endometrial protein: a marker for monitoring human endometrial function". Adv Exp Med Biol 1986; 230:167–86.

Julkunen et al. Identification by hybridization histochemistry of human endometrial cells expressing mRNA's encoding a uterine β-lactoglobulin homologue and an insulin-like growth factor binding protein-1. Mol Endocrinol 1990; 4:700–7.

Julkunen et al. Complete amino acid sequence of human placental protein 14: a progesterone-regulated uterine protein homologus to beta-lactoblobulins. Proc. Natl Acad Science USA 1988; 85:8845–49.

Knudsen, "Proteins transferred to nitrocellulose as immunogens". 1985; Anal Biochem 147:285–288.

Koistinen et al. Placental protein 12 is a decidual protein that binds somatomedin and has an identical N-terminal amino acid sequence with somatomedin-binding protein from human amniotic fluid. Endocrinology 1990; 118:1475–8.

Lafrenie et al, Tat Protein promotes chemotaxis and invasive behavior by monocytes. J. Immunol. 1196; 157:974–7.

Lifsey et al, "Isolation, characterization and immunohistochemical localization of bovine trophoblast protein-1" Biol Reprod, 40:343–52 (1989).

Lindley, "Life and death before birth" Editorial, Nature, 280:635–7 (1979).

Maslar and Riddick, "Prolactin production by human endometrium during the normal menstrual cycle". 1979. Am J Obstet Gynecol 1979; 135:751–4.

Matrisian et al, "Metalloproteinases expression and hormonal regulation during tissue remodeling in the cycling human endometrium" in Extracellular Matrix in the Kidney, 107:94–100, Koide H. Hayashi, T (eds) Contrib. Nephrol. Basel, Karger (1994).

McRae et al. Immunohistochemical identification of prolactin and 24K protein in secretory endometrium. Fertil Steril 1986; 45:643–48.

Mulholand and Villie, "Proteins synthesized by the rat endometrium during early pregnancy" J Reprod Fertil, 72:395–400 (1984).

Navot et al, "Hormonal manipulation of endometrial maturation" J Clin Endocrinol Metabol, 68:801–7 (1989).

O'Neill et al, "A bioassay for embryo derived platelet-activating factor as a means of assessing quality and pregnancy potential of human embryos" Fertil Steril, 47:969 (1987).

O'Neill et al, "Maternal blood platelet physiology and luteal phase endocrinology as a means of monitoring pre- and post-implantation embryo viability following in vitro fertilization" J In Vitro Fertil Embryo Transfer, 2:87–93 (1985).

Osteen et al. Development of a method to isolate and culture highly purified populations of stromal and epithelial cells from human endometrial biopsy specimens. Fertil Steril 1989; 52:965–72.

Paulson et al, "Embryo implantation after human in vitro fertilization: importance of endometrial receptivity" Fertil Steril, 53:87–4 (1990).

Psychoyos, "Endocrine control of egg implantation" in Handbook of Physiology, 187–215 Greep RO, Astwood EG, Geiger SR (eds), Washington, D.C., American Physiological Society, (1973).

Riitten, "Serous ovarian cyst fluids contain high levels of endometrial placental protein 14". Tumor Biol 1992; 13:175–9.

Roberts, "Conceptus interferons and maternal recognition of pregnancy" [Review] Biol Reprod, 40:449–52 (1989).

Roberts and Bazer, "The properties, function and hormonal control of uteroferrin, the purple protein of the pig uterus" in Steroid Induced Proteins, p. 133, edited by M. Beato, Holland, Amsterdam Elsevier-North (1980).

Roberts and Loewe, "Where have all the conceptus gone?" Lancet, 1:498–501 (1975).

Roberts et al, "Interferons at the placental interface" [Review] J Reprod Fertil, 41:63–74 (Supp, 1990).

Rodgers et al, "Patterns of matrix metalloproteinase expression in cycling endometrium imply differential functions and regulation by steroid hormones" J Clin Invest, 94:946–53 (1994).

Safro et al, "Elevated luteal phase estradiol:progesterone ratio in mice causes implantation failure by creating a uterine environment that suppresses embryonic metabolism" Fertil Steril, 54:1150–3 (1990).

Seppala et al, "Human endometrial protein secretion relative to implantation" Bailliere's Clinic Obstet Gynecol, 5:61–72 (1991).

Seppala et al, "Rutanen: uterine proteins, nomenclature determined by biological action" Res in Reprod, 19:2 (1987).

Seppala et al. Endometrial proteins: A reappraisal. Hum Reprod 1992; 7:31–8.

Sharma et al, "Influence of superovulation on endometrial and embryonic development" Fertil Steril, 53:822–9 (1990).

Sharpe et al. Detection of a progesterone-induced secretory protein synthesized by the uteri but not the endometriotic implants of rats with induced endometriosis. Fertil Steril 1991; 55:403–10.

Sharpe et al. Proliferative and morphogenic changes induced by the coculture of rat uterine and peritoneal cells: a cell culture model for endometriosis. Fertil Steril 1992; 58:1220–9.

Sharpe and Vernon. Polypeptides synthesized and released by rat endometriotic tissue differ from those of the uterine endometrium in culture. Biol Reprod. 1993a; 48:1334–1340.

Sharpe et al. Polypeptides synthesized and released by human endometriosis tissue differ from those of the uterine endometrium in cell and tissue explant culture. Fertil Steril 1993b; 60:839–51.

Sharpe et al. Synthesis and secretion of the progesterone-induced uterine protein, PUP-1, during early pregnancy in the rat. Soc Study of Reprod, 1993; P-233, Fort Collins, Col.

Sharpe et al. Immunolocalization of progesterone-induced uterine protein, PUP-1, in human endometrium and in endometrial epithelial and stromal cell cultures. Soc Study Reprod, 1994; P-26, Ann Arbor, Mich.

Sharpe and Zimmer, "Effects of the progesterone antagonist Onapristone (ZK 98.299) on synthesis and secretion of the progesterone uterine protein, PUP-1, in the rat" Amer Fertil Soc, p. 271, Montreal, Quebec, Canada (1993).

Sharpe et al, "Rapid regression of endometriosis by a new gonadotropin-releasing hormone antagonist in rats with surgically induced disease" in Current Concepts in Endometriosis, p. 449, edited by DP Chada and VC Buttram, Alan R. Liss, Inc., New York (1990a).

Sharpe et al, "Follicular atresia and infertility in rats treated with a gonadotropin-releasing hormone (GnRH) antagonist" Endocrinology, 127:25–31, (1990b).

Sharpe-Timms et al, "Immunolocalization of Progesterone-Induced Uterine Protein-1, PUP-1, in human endometrium during the menstrual cycle and in the placenta throughout gestation" Am J Obstet Gynecol, 173:1569–78 (1995).

Smith, "Growth factors in the human endometrium" Human Reproduction Update, 9:936–46 (1994).

Tabibzadeh, "Cytokines and the hypothalamic-pituitary-ovarian-endometrial-axis" Human Reproduction Update, 9:947–67 (1994).

Wahlstrom and Seppala. Placental protein 12 (PP12) is induced in the endometrium by progesterone. Fertil Steril 1984; 41:781–4.

Weibel, "Stereological Methods". In: Practical Methods for Biological Morphometry, Vol 1, New York: Academic Press; 1979:33–45.

Woessner, "Matrix metalloproteinases and their inhibitors in connective tissue remodeling" FASEB, 5:2145–54 (1991).

What is claimed is:

1. A method of monitoring effects of a treatment protocol to induce ovarian hyperstimulation or ovulation induction on uterine receptivity in a patient comprising:

(a) obtaining an uterine fluid or endometrial biopsy sample from the patient receiving treatments to induce ovarian hyperstimulation or ovulation induction on at least one of days 18–24 of a reproductive cycle; and (b) detecting a level and/or distribution of progesterone-induced uterine protein-1 (PUP-1) glycoprotein in the sample, wherein the PUP-1 glycoprotein is characterized by:

(I) being a progesterone induced and estradiol inhibited secretory glycoprotein specifically from stromal cells of endometrial origin;

(ii) having a molecular weight of 70,000 daltons as determined by two-dimensional sodium dodecyl sulphate polyacrylamide gel electrophoresis;

(iii) having an isoelectric point of 5.7; and (iv) being synthesized by human endometrium at times of the reproductive cycle which coincide with fertilization, early embryogenesis, and implantation; and wherein an altered distribution of the PUP-1 glycoprotein in the biopsy sample relative to that detected in normal receptive controls, and/or a decreased level of the PUP-1 glycoprotein in the sample relative to that detected in samples of uterine fluid or endometrial biopsy from normal receptive controls, and/or a level of the PUP-1 glycoprotein in the sample substantially the same as that detected in samples of uterine fluid or endometrial biopsy from non-receptive controls indicate that the treatment protocol may be disrupting uterine receptivity in the patient.

2. The method of claim 1 wherein the PUP-1 glycoprotein has an N-terminal amino acid sequence as set forth in SEQ ID NO: 1.

3. The method of claim 1 wherein the level or distribution of the PUP-1 glycoprotein is detected by immunoassay.

4. The method as set forth in claim 1 wherein the protocol to induce ovarian hyperstimulation or ovulation induction is selected from the group consisting of clomiphene citrate and gonadotropin stimulation.

* * * * *